US012484998B2

(12) United States Patent
Leighton et al.

(10) Patent No.: US 12,484,998 B2
(45) Date of Patent: Dec. 2, 2025

(54) CLEANING, HEALING AND REGENERATION OF TISSUE AND WOUNDS

(71) Applicant: SLOAN WATER TECHNOLOGY LIMITED, London (GB)

(72) Inventors: Timothy Leighton, Southampton (GB); David Voegeli, Southampton (GB); Christopher Harling, Southampton (GB); Thomas Secker, Southampton (GB); Craig Dolder, Southampton (GB); Mengyang Zhu, Southampton (GB)

(73) Assignee: SLOAN WATER TECHNOLOGY LIMITED, London (GB)

(*) Notice: Subject to any disclaimer, the term of this patent is extended or adjusted under 35 U.S.C. 154(b) by 1539 days.

(21) Appl. No.: 16/619,690

(22) PCT Filed: Jun. 4, 2018

(86) PCT No.: PCT/EP2018/064659
§ 371 (c)(1),
(2) Date: Dec. 5, 2019

(87) PCT Pub. No.: WO2018/228848
PCT Pub. Date: Oct. 20, 2018

(65) Prior Publication Data

US 2020/0164194 A1 May 28, 2020

(30) Foreign Application Priority Data

Jun. 5, 2017 (GB) ..................................... 1708901

(51) Int. Cl.
*A61C 17/20* (2006.01)
*A61C 17/024* (2006.01)
(Continued)

(52) U.S. Cl.
CPC ............ *A61C 17/20* (2013.01); *A61C 17/024* (2019.05); *A61D 5/00* (2013.01); *A61M 3/0204* (2014.02);
(Continued)

(58) Field of Classification Search
CPC ............ A61M 37/0092; A61M 3/0204; A61M 3/022; A61M 3/0233; A61M 3/0279;
(Continued)

(56) References Cited

U.S. PATENT DOCUMENTS 2,098,272 A * 11/1937 Benson .................. A61H 9/005 74/567
2,751,783 A 6/1956 Erdman
(Continued)

FOREIGN PATENT DOCUMENTS

AU 2018285022 B2 11/2021
CA 3182407 A1 12/2021
(Continued)

OTHER PUBLICATIONS

International Search Report for related International Application No. PCT/EP2018/064659; report dated Jan. 7, 2019; (6 pages).
(Continued)

*Primary Examiner* — Andrew J Mensh
*Assistant Examiner* — Nhu Q. Tran
(74) *Attorney, Agent, or Firm* — Banner & Witcoff, Ltd.

(57) ABSTRACT

A method of treating human or animal tissue, the method comprising the step of: i. directing a stream of an aqueous liquid comprising gas bubbles excited by acoustic energy towards a wound or anatomical pocket in human or animal tissue, or towards an anatomical space or potential space in human or animal tissue, or towards soft or hard tissue in an oral cavity or elsewhere in the human or animal body, or towards tissue in a nasal cavity, or towards tissue associated
(Continued)

with sinuses, eye, ear, digestive and genito-urinary systems, thereby to treat the human or animal tissue with the stream. The output stream can clean a wound in human or animal tissue, and can treat the wound by healing the wound, for example by stimulating fibroblasts in the wound tissue and causing, promoting or enhancing re-epithelialisation of epidermal tissue in the wound.

20 Claims, 12 Drawing Sheets

(51) Int. Cl.
*A61D 5/00* (2006.01)
*A61M 1/00* (2006.01)
*A61M 3/02* (2006.01)
*A61M 35/00* (2006.01)
*A61M 37/00* (2006.01)

(52) U.S. Cl.
CPC .......... *A61M 3/022* (2014.02); *A61M 3/0233* (2013.01); *A61M 3/0279* (2013.01); *A61M 37/0092* (2013.01); *A61M 1/77* (2021.05); *A61M 1/85* (2021.05); *A61M 1/92* (2021.05); *A61M 1/94* (2021.05); *A61M 35/00* (2013.01); *A61M 2209/04* (2013.01); *A61M 2250/00* (2013.01)

(58) Field of Classification Search
CPC ............ A61M 1/77; A61M 1/85; A61M 1/92; A61M 1/94; A61M 35/00; A61M 2209/04
See application file for complete search history.

(56) References Cited

U.S. PATENT DOCUMENTS 3,405,916 A 10/1968 Carmichael
4,103,519 A 8/1978 Davidson
4,444,146 A 4/1984 De Witz et al.
4,507,969 A 4/1985 Djordjevic et al.
5,001,932 A 3/1991 Light et al.
5,368,054 A 11/1994 Koretsky et al.
5,690,145 A 11/1997 Kuklinski et al.
6,003,527 A 12/1999 Netsu et al.
6,162,738 A 12/2000 Chen et al.
6,230,722 B1 5/2001 Mitsumori et al.
6,916,296 B2 * 7/2005 Soring ............ A61B 17/22004 601/3
7,117,741 B2 10/2006 Klein et al.
7,165,563 B1 1/2007 Boyd et al.
8,075,503 B2 * 12/2011 Jaeb ........................ A61N 7/00 601/3
10,661,314 B2 5/2020 Birkin et al.
11,426,772 B2 8/2022 Birkin et al.
11,577,284 B2 2/2023 Leighton et al.
2003/0106566 A1 6/2003 Danese et al.
2006/0021642 A1 2/2006 Sliwa et al.
2006/0060991 A1 3/2006 Holsteyns et al.
2006/0191562 A1 8/2006 Nunomura et al.
2007/0062555 A1 3/2007 Chang et al.
2008/0017219 A1 1/2008 Franklin
2008/0209650 A1 9/2008 Brewer et al.
2010/0297346 A1 11/2010 Sawada et al.
2012/0227761 A1 * 9/2012 Leighton .................. B08B 3/12 134/1
2015/0044632 A1 2/2015 Bergheim
2016/0325028 A1 11/2016 Lock
2017/0080197 A1 * 3/2017 Paunescu ................ A61N 7/00
2017/0217794 A1 * 8/2017 Lipkens .................. C12N 1/02
2021/0139115 A1 5/2021 Birkin et al.
2021/0387237 A1 12/2021 Leighton et al.
2023/0311171 A1 10/2023 Leighton et al.

FOREIGN PATENT DOCUMENTS

CN 101428283 A 5/2009
CN 101621951 A 1/2010
CN 201744457 U 2/2011
CN 102553858 A 7/2012
CN 102574169 A 7/2012
CN 103357606 A 10/2013
CN 204972417 U 1/2016
CN 107835720 A 3/2018
CN 110891692 A 3/2020
DE 4111592 A1 10/1992
EP 0579275 A1 1/1994
EP 0839586 A2 5/1998
EP 1600088 A1 11/2005
EP 3009202 A 4/2016
EP 3009202 A2 * 4/2016 .............. B08B 3/10
FR 2593090 A1 7/1987
GB 2516652 A 2/2015
GB 2538276 B 5/2017
GB 2569136 A 6/2019
GB 2563212 B 1/2020
IN 536979 5/2024
JP 644285 1/1989
JP H3264682 A 11/1991
JP H0731939 A 2/1995
JP H08290211 A 11/1996
JP H0924351 A 1/1997
JP H09287990 A 11/1997
JP 2001245381 A 9/2001
JP 2004082038 A 3/2004
JP 2004167377 A 6/2004
JP 2005058804 A 3/2005
JP 2005093873 A 4/2005
JP 2005296884 A 10/2005
JP 2007311756 A 11/2007
JP 2008119642 A 5/2008
JP 2009525867 A 7/2009
MX 2019014679 A 11/2020
NZ 760615 A 11/2021
RU 2565705 C2 10/2015
SU 929236 A1 5/1982
WO 2009037930 A1 3/2009
WO 2011023746 A2 3/2011
WO 2016180978 A1 11/2016
WO 2018228848 A2 12/2018
WO 2019110771 A1 6/2019
WO 2021250645 A3 2/2022

OTHER PUBLICATIONS

Written Opinion for related International Application No. PCT/EP2018/064659; report dated Jan. 7, 2019; (9 pages).
Jun. 18, 2021 (NZ) Patent Examination Report 2—App 760615.
Sep. 28, 2021—(CN) Office Action—App 201880047070.9.
Mar. 16, 2023—(EP) Examination Report—App 18738198.3.
Jun. 13, 2023—(MX) Office Action—App MX/a/2019/014679.
Apr. 22, 2022—(CN) Rejection Decision—App 201880047070.9.
Mar. 13, 2019—(WO) International Search Report and Written Opinion—App PCT/EP2018/083892.
M. Salta et al., "Bubbles versus biofilms: a novel method for the removal of marine biofilms attached on antifouling coatings using an ultrasonically activated water stream", Surface Topography: Metrology and Properties, 4 (2016) 034009; 11 pages; iopscience.iop.org.
Aug. 20, 2015—(GB) Search Report—App GB1508167.2.
Nov. 14, 2017—(WO) IPRP—App PCT/2016/060911.
Oct. 17, 2016—(WO) ISR & WO—App PCT/EP2016/060911.
Nov. 24, 2020—(AU) Examination Report No. 1—App 2018285022.
Nov. 25, 2020 (NZ) Patent Examination Report 1—App 760615.
Jan. 22, 2020—(EP) Office Action—App 18738198.3.
Jan. 15, 2016 (EP) Search Report—App 15196928.4.
Dec. 24, 2009—(GB) Search Report—App GB0914836.2.
May 5, 2011—(WO) International Serch Report—App PCT/EP2010/062448.

(56) References Cited

OTHER PUBLICATIONS

Jan. 14, 2015—(CN) Office Action—App 201080045751.5 (Eng trans).
Aug. 15, 2014 (JP) Office Action—App 2012-526053 (Eng Trans).
Sep. 23, 2014—(RU) Office Action—App 2012111316—(partial Eng trans).
Jan. 26, 2016—(EP) Partial Serach Report—App 15196928.4.
Dec. 17, 2020—(CN) Office Action—App 201680041121.8 (Eng trans).
Jan. 21, 2021—(CN) Office Actin—App 201880047070.9.
Aug. 19, 2024—(EP) Second Rule 71(3) Communication—App 18738198.3.
Feb. 29, 2024—(MX) 2nd Office Action—App MX/a/2019/014679.

* cited by examiner

Control

Saline

UAS

= 500 µm

CLEANING, HEALING AND REGENERATION OF TISSUE AND WOUNDS

The present invention relates to an apparatus for, and a method of, for treating human or animal tissue. The present invention also relates to a method of generating a liquid stream for treating a surface. The present invention further relates to a method of treating a wound or anatomical pocket or anatomical space or potential space in human or animal tissue, soft or hard tissue in the oral cavity, or tissue in the nasal cavity, for example for healing wounds and regenerating healthy tissue in a wound.

It is known from WO-A-2011/023746 to provide a cleaning method and apparatus in which cleaning of a surface is achieved by the employment of bubble action on a surface, or within a crevice within a surface, driven by acoustic stimulation. The method provides gas bubbles at the surface and employs modulated acoustic energy to generate surface waves in the bubbles to cause non-inertial cavitation of the bubbles. Such a bubble action enhances cleaning of the surface. A stream of liquid containing gas bubbles excited by acoustic energy is directed at the surface to be cleaned.

WO-A-2016/180978 discloses a modified cleaning method and apparatus in which cleaning of a surface is also achieved by the employment of bubble action on a surface driven by acoustic stimulation, but rather than using a stream of liquid, a body of liquid is retained against the surface to be cleaned, and acoustically excited gas bubbles in the body of liquid are directed against the surface to be cleaned.

Although WO-A-2011/023746 and WO-A-2016/180978 disclose that a wide range of surfaces may be cleaned by acoustically excited gas bubbles, there is still a need for further applications employing bubble action driven by acoustic stimulation to treat a surface, or a crevice within a surface.

The present invention aims at least partially to provide this need.

The present invention provides an apparatus for treating human or animal tissue, the apparatus comprising a conical body defining a chamber, the conical body extending between a base of the conical body and an outlet nozzle of the conical body, wherein the base has an inlet for liquid flow into the chamber and the outlet nozzle is at a conical tip of the conical body and is configured to generate an output stream of liquid flow from the chamber for treating human or animal tissue, an acoustic transducer associated with the conical body to introduce acoustic energy into the liquid within the chamber whereby the acoustic energy is present in the output stream, and a gas bubble generator for providing gas bubbles in the output stream, the gas bubbles in the output stream being excited by the acoustic energy, wherein the conical body and the nozzle thereof have a pressure amplitude reflection coefficient with respect to the acoustic energy in water within the chamber of from −0.95 to −1.0, a liquid supply system adapted to supply a liquid flow through the inlet at a flow rate of from 0.1 to 7 litres/minute, the outlet nozzle is configured to generate an output stream of liquid flow having an average width of from 0.25 to 20 mm, the acoustic transducer is configured to generate acoustic energy having a frequency of from 0.1 to 5 MHz and the gas bubble generator is configured to provide in the output stream bubbles having a radius of from 0.5 to 40 μm.

The present invention further provides an apparatus for treating human or animal tissue, the apparatus comprising a conical body defining a chamber, the conical body extending between a base of the conical body and an outlet nozzle of the conical body, wherein the base has an inlet for liquid flow into the chamber and the outlet nozzle is at a conical tip of the conical body and is configured to generate an output stream of liquid flow from the chamber for treating human or animal tissue, an acoustic transducer associated with the conical body to introduce acoustic energy into the liquid within the chamber whereby the acoustic energy is present in the output stream, a gas bubble generator for providing gas bubbles in the output stream, the gas bubbles in the output stream being excited by the acoustic energy, and a cup member having a closed end fitted to the outlet nozzle of the conical body, the cup member defining a second chamber and being configured to receive the output stream into the second chamber from the closed end, the cup member having an open end with an annular rim configured to form an annular contact against human tissue.

The present invention further provides an apparatus for producing a liquid including acoustically excited gas bubbles, the apparatus comprising a body defining a chamber, the body having an inlet for liquid flow into the chamber and an outlet for liquid including acoustically excited gas bubbles, an acoustic transducer associated with the body to introduce acoustic energy into the liquid within the chamber, a gas bubble generator for providing gas bubbles in the liquid within the chamber, the gas bubbles in the liquid being excited by the acoustic energy, and a gas removal device coupled to the inlet for removing gas from a liquid supply to the apparatus, the gas removal device comprising a casing having a input for liquid and an output for liquid, and a plurality of compartments serially located between the input and output which define a serpentine path therebetween, at least one of the compartments including a headspace at an upper part thereof for collecting gas released from liquid flowing along the serpentine path The present invention further provides a method of generating a liquid stream for treating a surface, the method comprising the steps of:

a. providing a conical body defining a chamber, the conical body extending between a base of the conical body and an outlet nozzle at a conical tip of the conical body;
b. inputting a flow of aqueous liquid into the chamber through an inlet at the base and generating an output stream of liquid flow from the chamber through the outlet nozzle, the output stream having a liquid flow rate of from 0.1 to 7 litres/minute, and the output stream having an average width of from 0.25 to 20 mm;
c. providing gas bubbles in the output stream, the gas bubbles having a radius of from 0.5 to 40 μm;
d. introducing acoustic energy having a frequency of from 0.1 to 5 MHz into the liquid within the chamber whereby the acoustic energy is present in the output stream and excites the gas bubbles; and
e. directing the output stream comprising the acoustically excited gas bubbles and acoustic energy towards a surface to be treated.

The present invention further provides a method of generating a liquid stream for treating a surface, the method comprising the steps of:

a. providing a conical body defining a chamber, the conical body extending between a base of the conical body and an outlet nozzle at a conical tip of the conical body, wherein a closed end of a cup member is fitted to the outlet nozzle of the conical body, the cup member defines a second chamber, and the cup member has an open end with an annular rim which is disposed against a surface to be treated;

b. inputting a flow of aqueous liquid into the chamber through an inlet at the base and generating an output stream of liquid flow from the chamber through the outlet nozzle and into the second chamber from the closed end;

c. providing gas bubbles in the output stream;

d. introducing acoustic energy into the liquid within the chamber whereby the acoustic energy is present in the output stream and excites the gas bubbles; and e. directing the output stream comprising the acoustically excited gas bubbles and acoustic energy towards a surface to be treated.

The present invention further provides a method of treating human or animal tissue, the method comprising the step of: i. directing a stream of an aqueous liquid comprising gas bubbles excited by acoustic energy towards a wound or anatomical pocket in human or animal tissue, or towards an anatomical space or potential space in human or animal tissue, or towards soft or hard tissue in an oral cavity or elsewhere in the human or animal body, or towards tissue in a nasal cavity, or towards tissue associated with sinuses, eye, ear, digestive and genito-urinary systems, thereby to treat the human or animal tissue with the stream.

The present invention yet further provides an aqueous liquid comprising gas bubbles excited by acoustic energy for use in wound healing in human or animal tissue.

Optional or preferred features are defined in respective dependent claims.

The present invention is at least partly predicated on the finding by the present inventors that a stream of liquid containing gas bubbles excited by acoustic energy can be provided with specific parameters, such as liquid flow rate, average width of the stream of liquid flow, acoustic energy frequency and gas bubble radius, to enable the stream of liquid containing the acoustically excited gas bubbles to be applied to human or animal tissues with the effect that therapeutic effects are achieved.

In particular, it has been found by the present inventors that such a liquid stream can provide the technical effect of cleaning wounds and anatomical pockets or anatomical space or potential space in human or animal tissue. The present invention can also clean soft and hard tissue in the oral cavity and tissue in the nasal cavity. In this context, the term ‘cleaning’ in this specification encompasses both the removal of inactive contaminants, such as small particles, and the removal of active contaminants, such as microbes, biofilms, and chemicals that interact with tissue. Most particularly, it has been found that such a liquid stream can provide the technical effect of the disruption of biofilms on human or animal tissue, particularly within wounds and anatomical pockets or anatomical space or potential space.

Furthermore, it has been surprisingly found by the present inventors that there is additional healing of tissue and wounds over and above that healing which follows from cleaning. That is to say, whilst the presence of a contaminant (such as a biofilm) hinders healing and this hindrance is reduced if the contaminant level is reduced, there is additional healing over and above that which comes from the removal of such a hindrance. That is to say, wounds and injured tissues that are kept free of contamination, heal better when treated by the device than control tissue that has been similarly kept free of contamination.

Furthermore, it has been found by the present inventors that such a liquid stream can provide the technical effect of promoting the healing of wounds in human or animal tissue and the formation of/return to normal healthy tissue and tissue regeneration. It has surprisingly been found that the output stream heals the wound by stimulating blast cells in tissue in the wound, and modulating biochemical mediators of wound healing, optionally wherein the wound is a wound in skin and the output stream heals the wound by stimulating dermal fibroblasts and keratinocytes in epidermal tissue in the wound and modulating mediators of tissue repair. For a wound in skin, the output stream heals the wound by causing, promoting or enhancing re-epithelialisation of epidermal tissue in the wound, and this may be achieved optionally by stimulating dermal fibroblasts and keratinocytes in epidermal tissue in the wound and modulating mediators of tissue repair.

It has been surprisingly found by the present inventors that although it is known in the prior art that ultrasound can be applied to certain classes of injury, such as bone microfractures, to achieve a therapeutic healing effect, the combination of ultrasound within a cleansing stream of liquid provides the ability to both clean and promote the formation of healing and tissue regeneration, as well as having the ability to disrupt and remove biofilm and can optionally have a direct bactericidal action, preventing biofilm reformation, which can be combined into a single treatment.

The present invention has particular application to wounds that have become infected, for example by bacteria or other micro-organism (e.g. fungi, parasites). The technology can clean away, and at times have a killing effect on, such microbes.

In this specification, the term ‘wound’ is herein defined as including (but is not restricted to) sites formed by the removal or transformation or inflammation of the normal human or animal tissue (epidermis, gum etc.) to produce abnormal exposure of underlying tissue, or transform healthy tissue into unhealthy tissue. Trauma, burning, sun exposure, cutting, the formation of ulcers and abscesses, disease (including gum disease) are all included. Specific circumstances would be abrasion or cutting or burning or solar exposure of the epidermis to expose the dermis; or damage to the gum.

In this specification, the term ‘anatomical pocket’ is herein defined as including (but is not restricted to) periodontal pockets, and cavities associated with the eye, the urinary-genital system, ears, and oral, nasal and digestive systems.

In some preferred embodiments of the present invention, the stream of liquid for therapeutic use can be chemical free, and may comprise or consist of water, optionally in the form of a conventional saline solution (i.e. by which, in this specification, is meant typically ‘normal saline’, which in this context means that the solution is approximately isotonic with human tissue fluid, or solution of sodium chloride 0.9% w/v), and may be free of biocides and/or drugs or other pharmaceutical compositions. The use of water or a saline solution reduces the risk of adverse reactions in tissue that can have been severely traumatized (e.g. burns), and also reduces the provision in waste of dilute forms of pharmaceuticals (such as antibiotics) which are known to contribute to the development of antibiotic resistance.

In alternative preferred embodiments of the present invention, gene therapy agents or chemical agents, for example biocides, antimicrobials, pharmacological agents to promote healing, and/or biochemical modulators, may optionally be added to the liquid, e.g. as agents in the bulk liquid, or the bubble, e.g. as agents carried in the bubble wall or gas. By combining such agents with the delivery system of the stream of liquid containing gas bubbles excited by acoustic energy, the penetration of such agents into a difficult-to-penetrate target region, for example crevices, contoured surfaces, biofilms and anatomical spaces such as dental root canals, an exemplar but not exhaustive list of the structures that are covered by the term 'difficult-to-penetrate target region', is increased when the bubbles are drawn into these surfaces by radiation forces. The penetration of the agents is further increased because the bubbles induce liquid convection by generating bubble-induced liquid motions associated with the wakes, boundary layer, and local circulations including microstreaming. This would, for example, 'pump' agents into regions such as 'difficult-to-penetrate target region' where normally the concentration of that species is lower than desirable, or takes a greater amount of time to penetrate, because it has previously relied upon diffusion. In this way, the bubbles employed in accordance with the present invention increase the penetration of these agents into the 'difficult-to-penetrate target region'.

The result is that greater and quicker penetration of the agents into the 'difficult-to-penetrate target region' can be achieved using the same concentration of the original agents, or the same concentration as before can be achieved at the base of the 'difficult-to-penetrate target region' using less of the agent at the source. As an example of the latter, if an agent is present in aqueous solution, and previously relied simply on diffusion to achieve the target concentration at a 'difficult-to-penetrate target region' (e.g. the base of a crevice), then the present invention allows the same concentration at the same inaccessible location to be achieved using a lower concentration of the agent in the bulk liquid outside of the 'difficult-to-penetrate target region'.

In the preferred embodiments of the present invention, the method and apparatus provide that the treatment of the human or animal tissue can be carried out during conventional medical procedures and does not require extensive additional medical training. In the method, a stream of liquid is directed towards the area of tissue to be treated, and this technique can be employed simply to replace the time taken for the clinician to conduct one action, such as a flush, rinse or wash, with an very similar amount of time conducted in a very similar manner, namely to direct a stream of liquid towards the area of tissue to be treated. However, it has been found by the present inventors that by providing the stream of liquid containing the acoustically excited gas bubbles which is applied to human or animal tissues, unexpected therapeutic effects are achieved. The incorporation into a stream of aqueous liquid of acoustically excited gas bubbles transforms a conventional flush, rinse or wash from a sometimes ineffective procedure, to a highly effective one, both in terms of cleaning and in terms of healing.

The preferred embodiments of the present invention provide an apparatus and method adapted to achieve treatment of human or animal tissue by the employment of bubble action on a surface, or within an anatomical pocket, such as a crevice, within a surface, driven by acoustic stimulation. This avoids inertial collapse at the surface and hence the associated erosion mechanisms of known ultrasonic cleaning systems and methods.

For the apparatus of the preferred embodiments of the present invention, the nozzle material and shape, and the driving acoustic frequency, may be chosen such that at least one mode is not evanescent in the liquid stream. The nozzle may be designed to prevent a strong impedance mismatch between the sound field in the conical body and the sound field in the liquid stream. When the liquid stream is surrounded by gas, such as atmospheric air, once it leaves the nozzle, it is preferred that material of the nozzle, and the conical body, are either exactly (or nearly) able to produce pressure-release reflection of sound from the liquid that is incident upon the material, or acoustically transparent (no reflection or attenuation) so that the sound field encounters a pressure-release condition when in contact with the atmospheric air. Furthermore, it is preferred if the shape of the cone and nozzle allows the perimeter of the pressure-release boundary to transition from the end of the cone that is remote from the nozzle, towards the nozzle, in a smooth manner without sudden changes in cross section; and furthermore, at the tip of the nozzle where the stream exits the nozzle, for the perimeter for the pressure-release boundary in the nozzle to match, as closely as possible, the perimeter of the stream where it exits the nozzle. The flow rate and nozzle design may be chosen so that the liquid stream does not lose integrity before it reaches the target surface to be cleaned and healed (e.g. break up into drops, entrain unwanted bubbles, etc.) to the extent that it hinders the transmission of sound from the nozzle to the target surface. The shape of the conical body may be designed to assist the transmission of sound from the cone to the liquid stream and subsequently through the nozzle. An amplitude or frequency modulated sound field may dramatically improve pressure transmission within the fluid flowing through the apparatus to the target surface.

Without being bound by theory, it is believed that in accordance with the preferred aspects of the present invention, the motion of the bubble process is dominated by the dynamic balance and imbalance of the oscillating pressure in the liquid and the oscillating pressure within the gas phase which results in non-inertial cavitation, rather than the converging momentum and inertia of the liquid which results in inertial collapse. The cleaning, healing and tissue regeneration can be further enhanced by the establishment of surface waves on the bubble wall (also sometimes referred to as bubble shape oscillations, of which the Faraday wave is the surface wave which, when the bubble is in pulsation resonance, requires the least acoustic pressure to stimulate). Therefore the apparatus and method of the present invention are preferably adapted to generate bubbles in the device at a location remote from, but close to, the solid/liquid interface of the surface to be treated and then to drive them against that surface with an appropriate sound wave sufficient to produce non-inertial cavitation and, if applicable, surface waves on the bubble wall. In addition to the stream flow, acoustic radiation forces may be effective at moving bubbles towards the tissue, and in particular can be effective at causing bubbles to penetrate crevices which other treatment methods (flow, wipes, brushes, etc.) can find difficult to penetrate.

A further feature of the preferred embodiments of the present invention is to deliver such treatment of human or animal tissue, using non-inertial cavitation, through a liquid stream, which avoids the need for immersion, and so makes the apparatus portable. This may be achieved by a suitable adaptation of existing cleaning systems which currently deliver a flow of liquid to generate cleaning, and healing and tissue regeneration. A portable apparatus may be battery driven. Such an apparatus of the preferred embodiments of the present invention system may also conserve water and/or power compared to a known immersion system.

In particular, the present invention is at least partly based on the findings by the present inventors that surface treatment (tissue cleaning, healing and regeneration) may be achieved through the generation of bubble oscillation (including surface waves) driven by appropriate acoustic excitation. Also, crevice cleaning may be achieved through bubble capture into pores and other surface features, including, but not restricted to, capture through processes of flow, hydrodynamic effects, or acoustic radiation forces. These bubbles oscillate and remove material from the crevice, and promote tissue regeneration and healing.

In the preferred embodiments of the present invention, the bubbles are generated, and then the bubbles flow, together with the flowing stream, towards a target tissue surface; the bubbles are not excited whilst they are in the stream, but only when the bubbles are on the tissue surface. If the bubbles are excited in the stream, they attenuate the sound field in the stream, and prevent the sound field effectively reaching the target tissue surface. Furthermore, if the sound field hits the bubbles when they are in the stream, before they reach the target, the sound field can cause the bubbles to coalesce with each other in the stream, which can prevent the combination of tissue cleaning, tissue regeneration and healing being effectively achieved.

It is well known that effective irrigation/cleansing of 'dirty' wounds (such as those caused by trauma) presents a particular challenge compared to simple wounds, due to the increased microbial contamination, tissue debris and irregularity of the wound shape (including small crevices).

Bubble population effects may be harnessed to allow transmission of sound down through the liquid to the surface to be cleaned, healed and regenerated. The flow apparatus, geometry, materials and acoustic characteristics of the bubble population (as well as its distribution in the liquid and how this varies in space and time) may allow efficient acoustic transfer to the surface to be cleaned, healed and regenerated.

Relatively low flow rates may be deployed, minimising cleaning solution wastage, and making the ingress of liquid more acceptable to the patient (e.g. dental patient), simplifying management of the run-off (e.g. in hospital wards), and reducing the dilution of the run-off. A run-off with a generally higher concentration of contaminants (e.g. microbes) is more facilitated for use in detecting the contaminants present in the run-off on a time scale that is rapid enough to allow for targeted therapy. The targeted therapy may, for example, comprise detecting the bacterial species that was present in the biofilm in an infected wound, and detecting any antibiotic resistances in that bacteria, so that a targeted and effective antibiotic can be delivered to the disrupted biofilm within the window (e.g. 24 hours) after disruption when the biofilm is particularly susceptible to the correct antibiotic, before the protective effect of the biofilm is re-established. However, it has been demonstrated that biofilm removed by the device fails to re-establish for over 24 hours following a single treatment.

Embodiments of the present invention will now be described by way of example only, with reference to the accompanying drawings, in which.

Figure 8A:
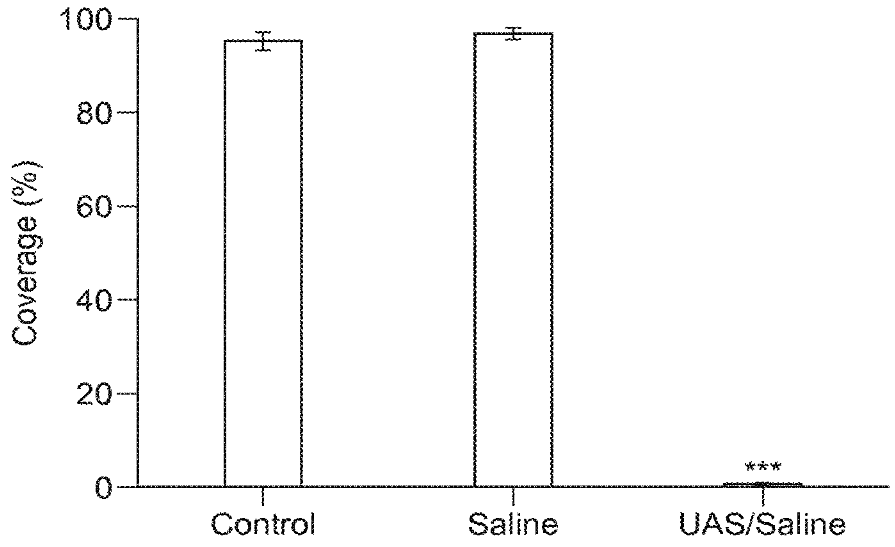
Figure 8B:
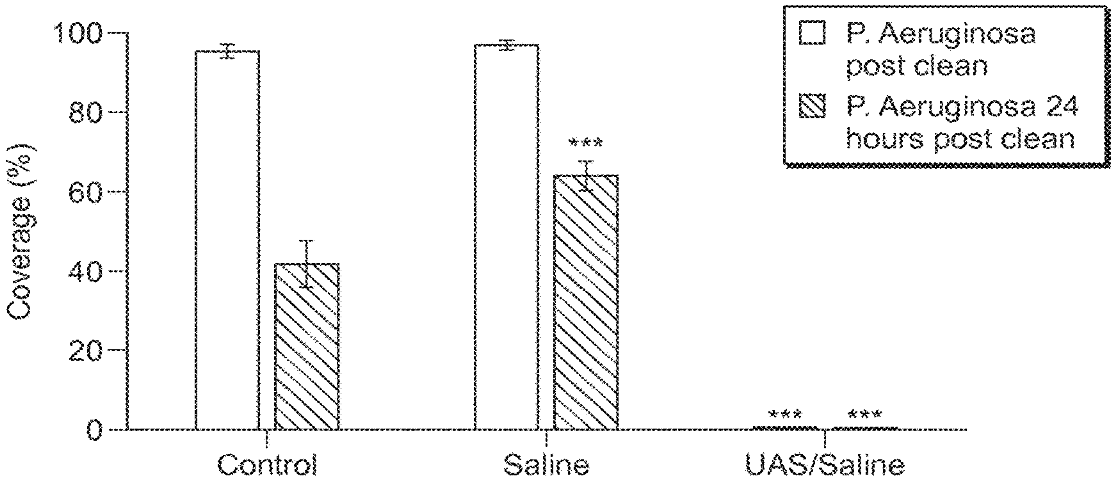
Figure 9A:
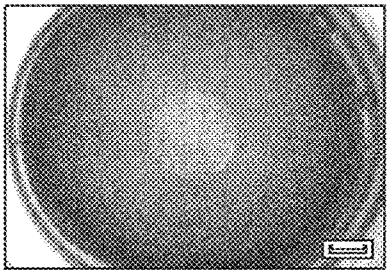
Figure 9B:
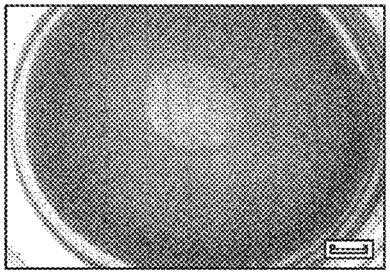
Figure 9C:
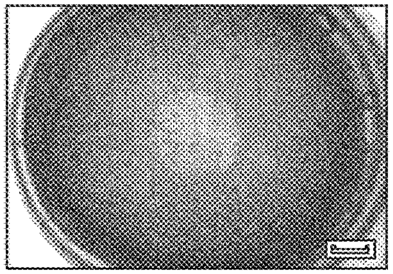
Figure 10:
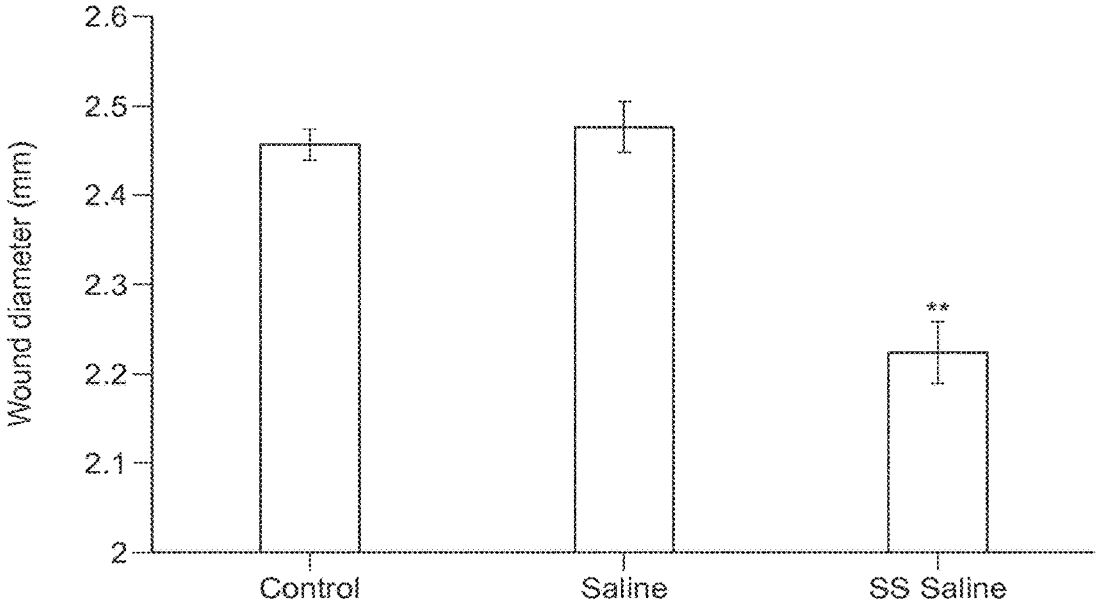
Figure 11A:
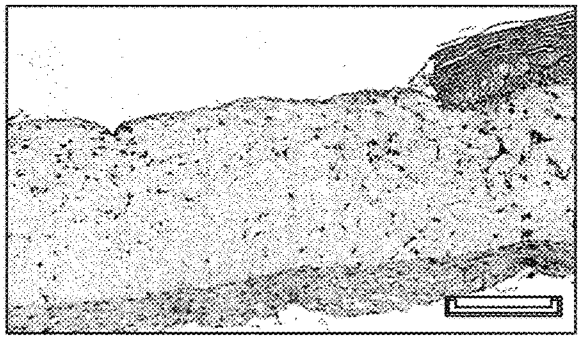
Figure 11B:
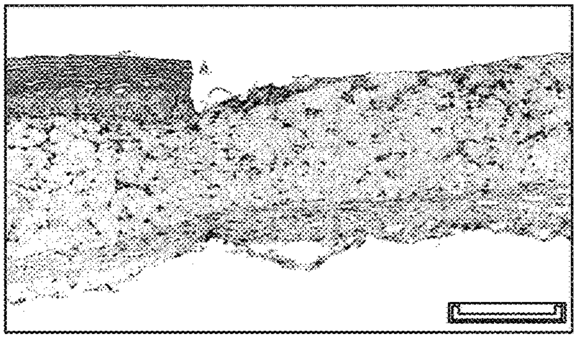
Figure 11C:
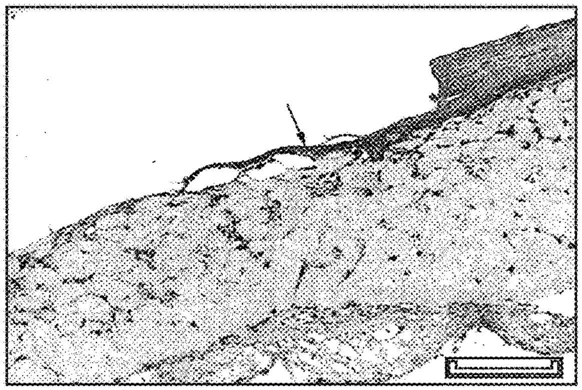
Figure 11D:
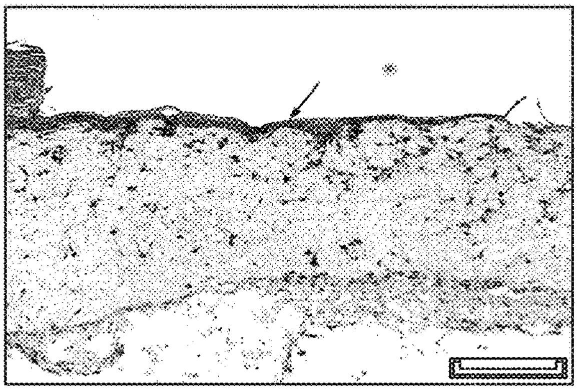
Figure 12:
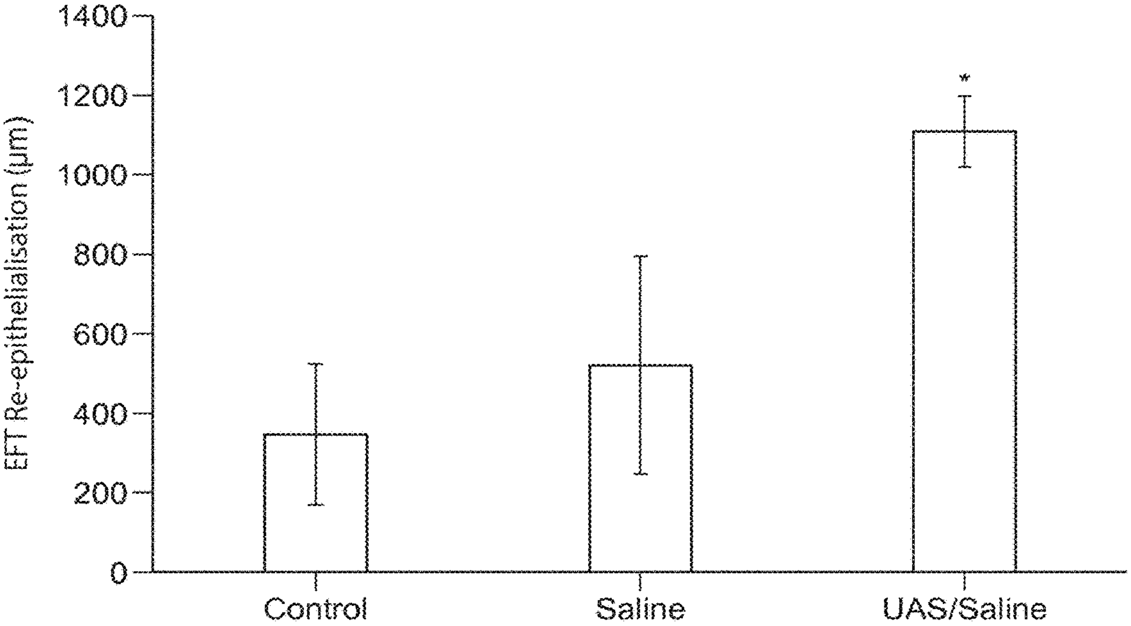
Figure 13A:
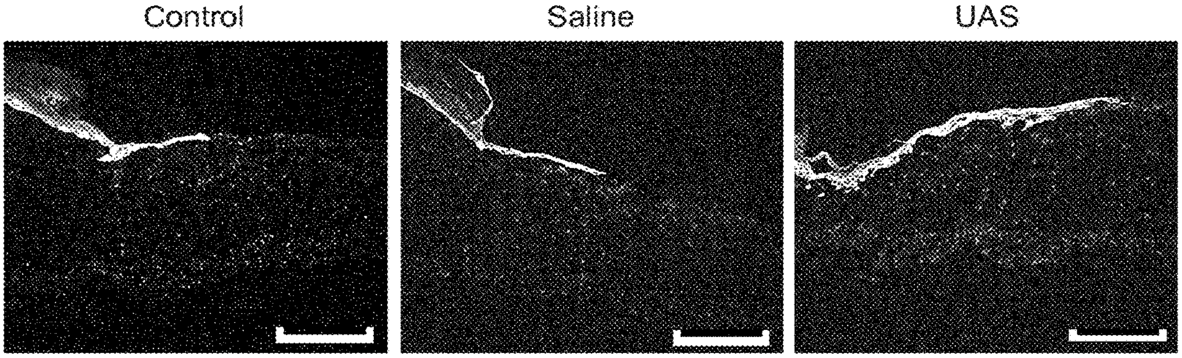
Figure 13B:
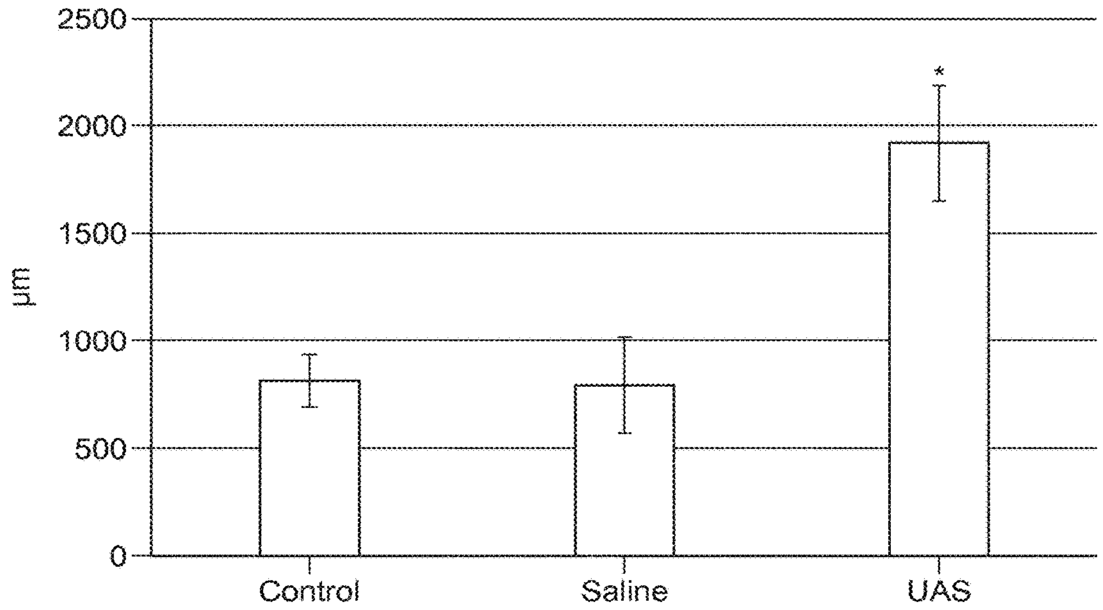
Figure 14:
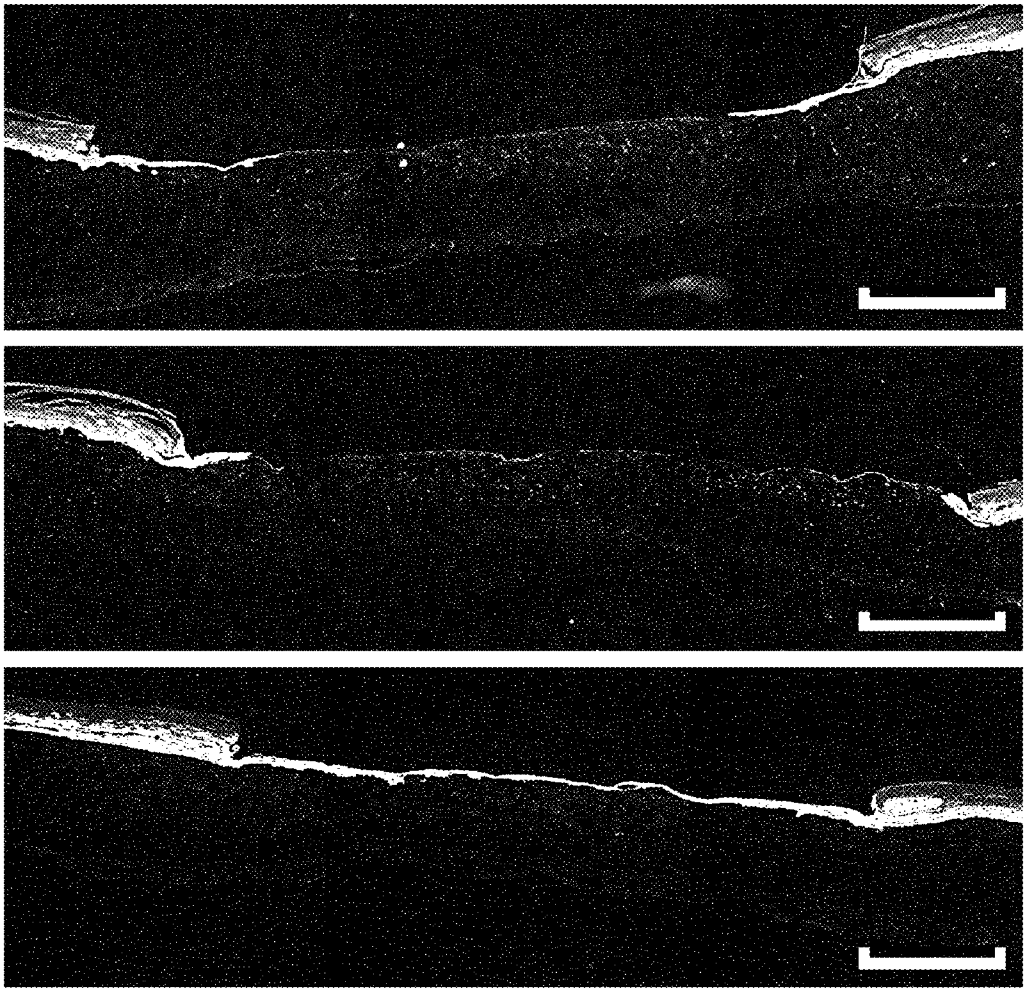
Figure 15A:
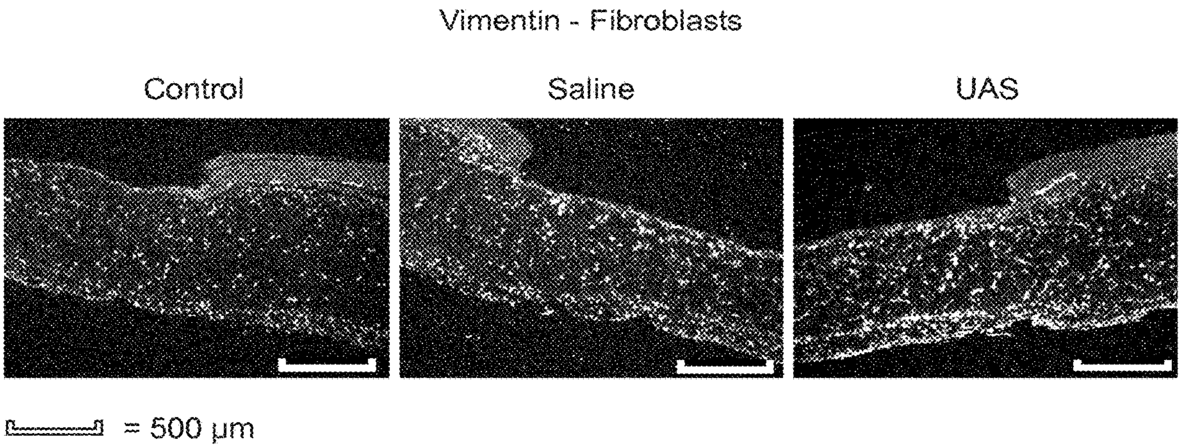
Figure 15B:
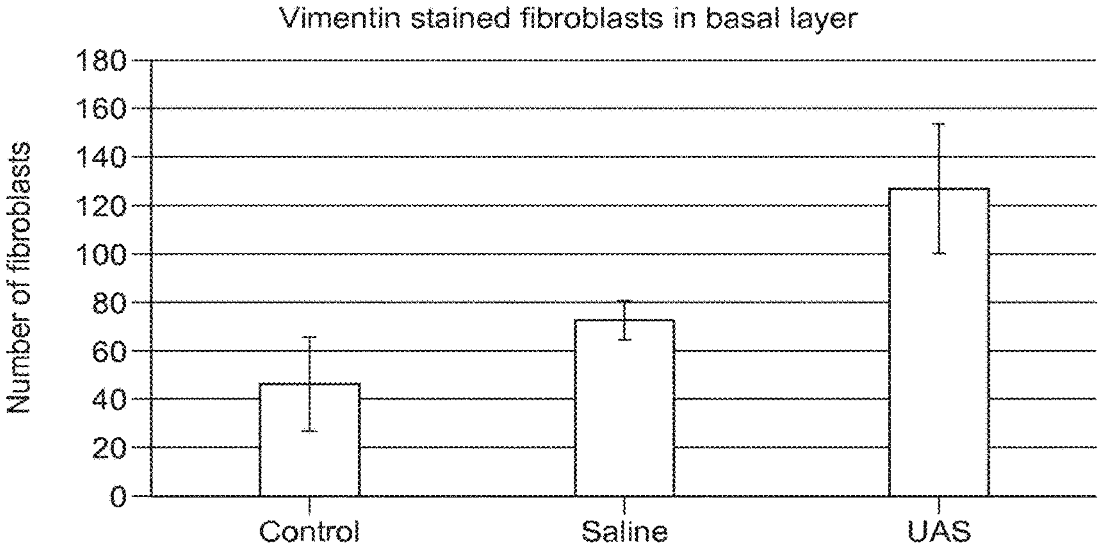
Figure 16:
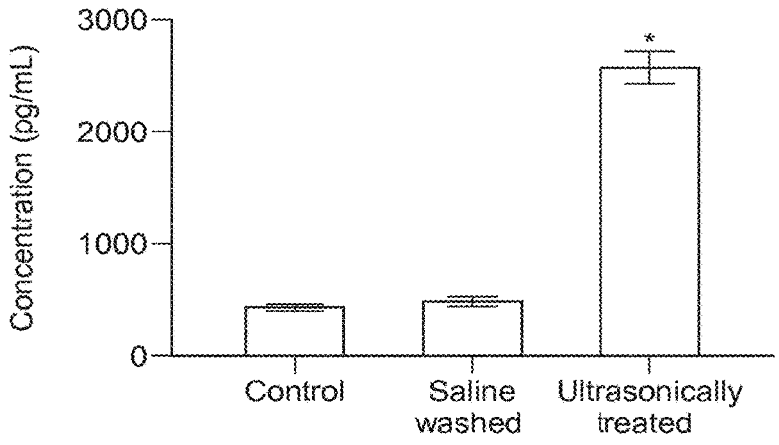
Figures 17A, 17B, 17C:
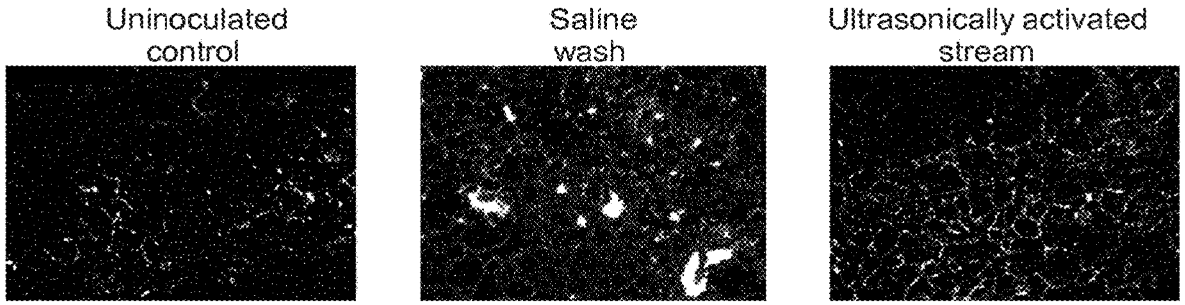
Figure 18:
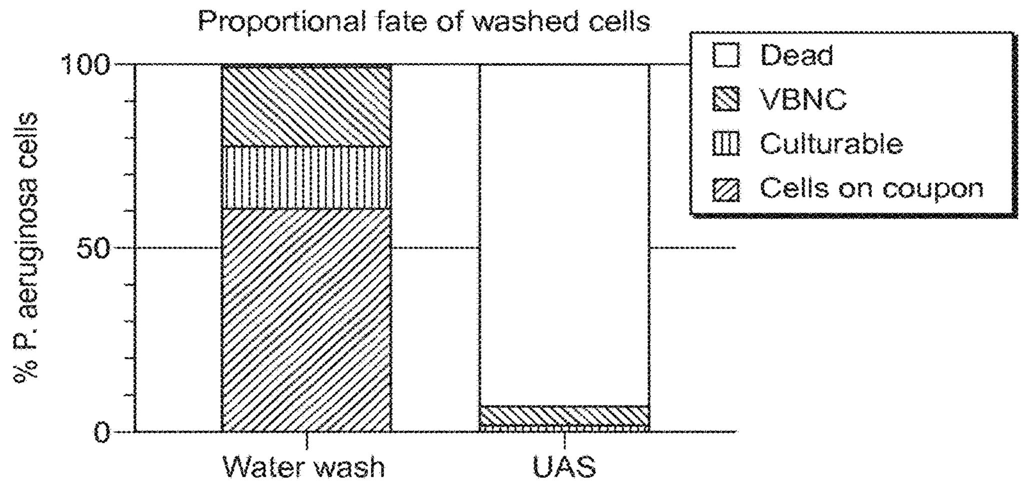
Figure 19:
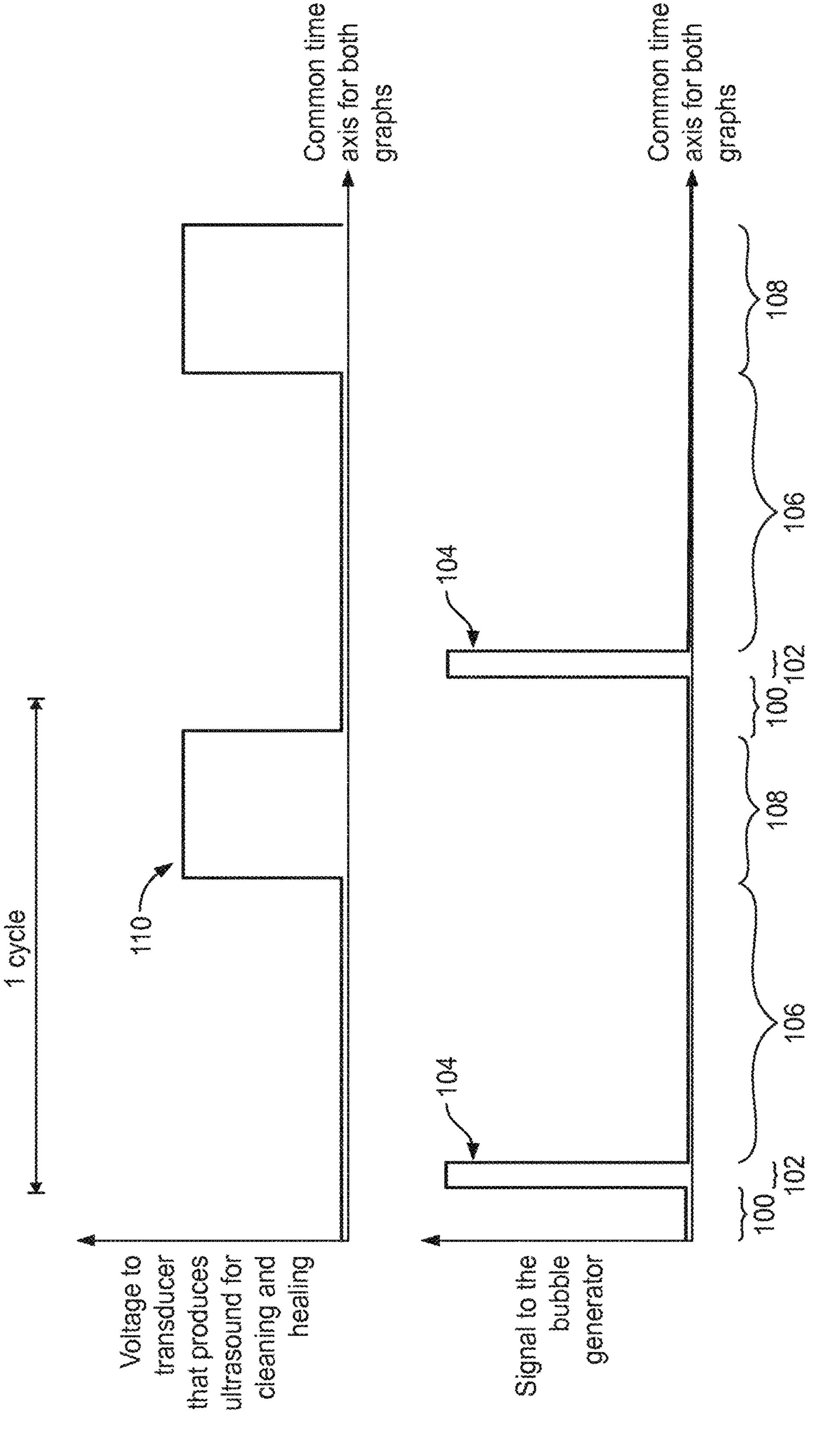
Figure 20:
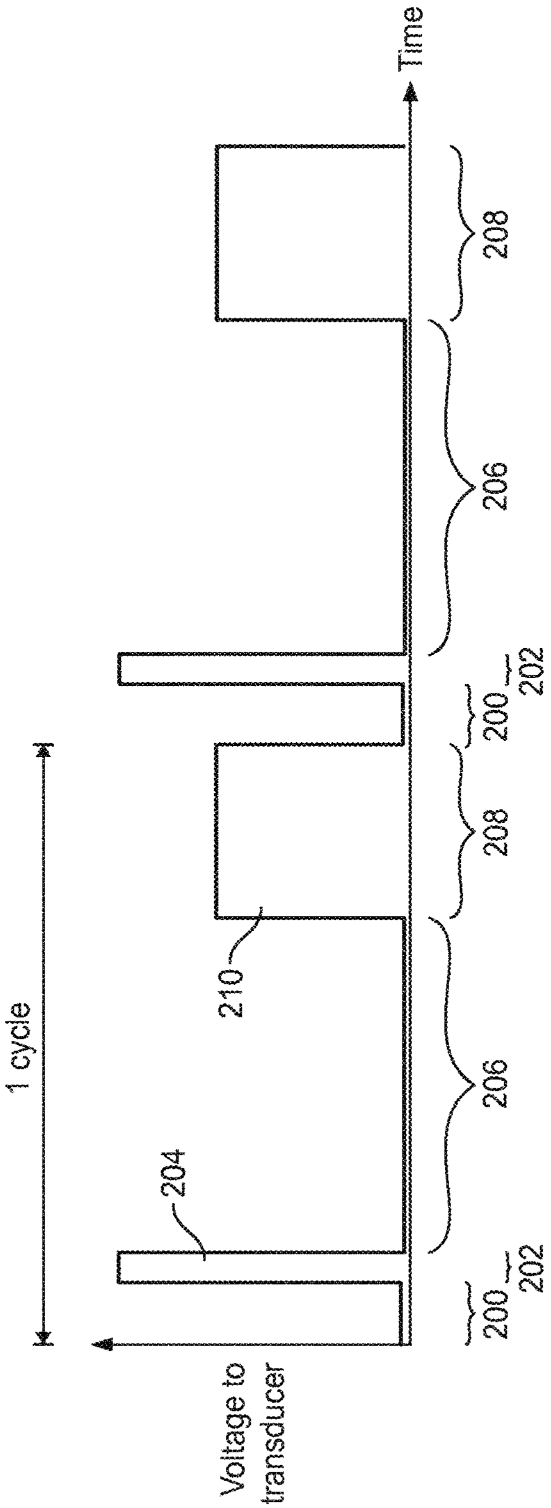

FIGS. 8(*a*) and 8(*b*) are graphs which show the percentage coverage of GFP tagged *Pseudomonas aeruginosa* pMF230 in situ detection from image analysis in wound models used in Example 1, FIG. 8(*a*) showing the coverage immediately after cleaning and FIG. 8(*b*) showing the coverage 24 hours after cleaning;

FIG. 9 illustrates micrographs which show wound healing in Epiderm full thickness wound models used in Example 2;

FIG. 10 is a graph which shows wound healing in the Epiderm full thickness wound models used in Example 2;

FIG. 11 illustrates micrographs which show Haematoxylin and Eosin (H&E) stained sections from the Epiderm full thickness wound models used in Example 2;

FIG. 12 illustrates micrographs which show the re-epithelialisation in the Epiderm full thickness wound models used in Example 2;

FIGS. 13(*a*) and (*b*) demonstrates the increased migration of keratinocytes across a wound bed seven days post-treatment with a cleaning, healing and tissue regeneration apparatus in accordance with an embodiment of the present invention, FIG. 13(*a*) showing micrographs and FIG. 13(*b*) showing a graph illustrating increased migration of keratinocytes;

FIG. 14 illustrates micrographs showing immunocytochemical staining for cytokeratin 14 demonstrating stimulation of keratinocyte migration across a wound after treatment with a cleaning, healing and tissue regeneration apparatus in accordance with an embodiment of the present invention;

FIGS. 15(*a*) and (*b*) illustrate the increased fibroblast activity observed in the dermo-epidermal junction of Epiderm full thickness (EFT) tissue samples seven days post-treatment with a cleaning, healing and tissue regeneration apparatus in accordance with an embodiment of the present invention, FIG. 15(*a*) showing micrographs and FIG. 15(*b*) showing a graph illustrating increased fibroblast numbers in the dermo-epidermal junction;

FIG. 16 is a graph showing modulation of matrix metalloproteinases, to demonstrate modulation of mediators to improve healing, after treatment with a cleaning, healing and tissue regeneration apparatus in accordance with an embodiment of the present invention;

FIG. 17 shows micrographs of *Pseudomonas aeruginosa* removal from stainless steel after treatment with a cleaning, healing and tissue regeneration apparatus in accordance with an embodiment of the present invention;

FIG. 18 is a graph which shows killing of *Pseudomonas aeruginosa* after treatment with a cleaning, healing and tissue regeneration apparatus in accordance with an embodiment of the present invention;

FIG. 19 illustrates a control protocol for the transducer when there is a separate bubble generator (e.g. by electrolysis, venturi, gas injection, ozone generation, microfluidics etc.) in an apparatus according to a further embodiment of the present invention; and FIG. 20 illustrates a control protocol for the transducer when the transducer additionally functions as the bubble generator in an apparatus according to a further embodiment of the present invention.

Figure 1:
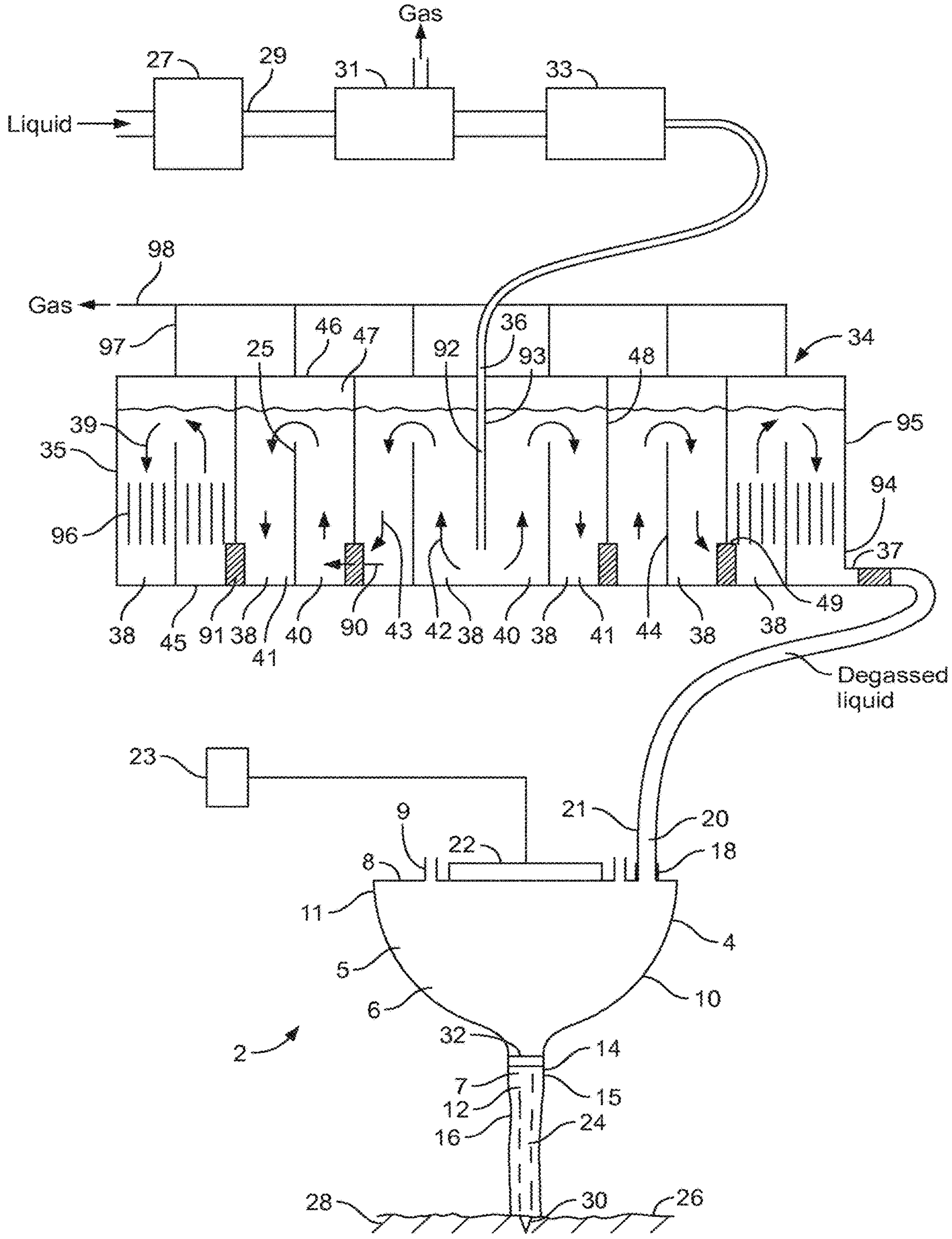
FIG. 1 is a schematic side view, not to scale, of a cleaning, healing and tissue regeneration apparatus in accordance with a first embodiment of the present invention.

Referring to FIG. 1, there is shown a cleaning, healing and tissue regeneration apparatus in accordance with a first embodiment of the present invention.

The cleaning, healing and tissue regeneration apparatus, designated generally as 2, comprises a hollow conical body 4 defining a central chamber 6. The body 4 has a rear wall 8 in a base 11 and a substantially conical wall 10 extending forwardly away therefrom which terminates in a forwardly-located orifice 12 in an outlet nozzle 14 of the conical body 4. The rear wall 8 also contains one or more vents 9 through which liquid containing any gas pockets can leave. Although use of an outgasser, as described below, should reduce the build-up of gas within the conical body 4, certain circumstances (for example, prolonged use, air leaks in the pump, insufficiently smooth pumping, variation in the gas content of the water coming from the source etc.) can cause gas to build up in the cone, and if this happens this needs to be periodically vented, most conveniently if the vent is place at the uppermost point of the liquid in the conical body 4 (e.g. in FIG. 1 that would be in the rear wall 8). Typically, both the substantially conical wall 10 and the outlet nozzle 14 are rotationally symmetric, i.e. circular, although other geometric shapes may be employed. In this specification the term ‘substantially conical’ should be interpreted broadly to encompass structures which are not only geometrically conical, and for example have a linear, convex or concave wall, but also structures which for example are bell-like, having a concave inner wall as seen from inside, or have a constant half-angle as shown, or are horn-like and have a convex inner wall as seen from the inside.

The nozzle 14 is at a conical tip 15 of the conical body 4 and defines a liquid outlet 16 in the form of an orifice. The base 11 has a liquid inlet 18 which is located at or adjacent to the rear wall 8. A liquid supply conduit 20, typically in the form of a flexible hose, communicates with the inlet 18 and comprises part of a liquid supply system 21. An acoustic transducer 22 is mounted on the rear wall 8. A controller 23 controls the operation of the transducer 22. Typically, the transducer 22 is mounted on an outer surface of the wall 8 and extends over a substantial proportion of the surface area of the wall 8. Alternatively, the transducer 22 may be embedded into the chamber 6 on or through the rear wall 8. The transducer 22 may be mounted elsewhere at a location associated with conical body 4 provided that the transducer 22 is configured to introduce acoustic energy into the liquid within the chamber 6 whereby the acoustic energy is present in an output stream from the nozzle 14.

The rear wall 8 comprises a plate, for example of plastic, such as polycarbonate, or a metal such as aluminium or stainless steel, having the liquid inlet 18 therein and on which the acoustic transducer 22 is mounted. The conical body 4 extends forwardly of the rear wall 8 and forms an integral nozzle 14. The walls of the conical body 4 and the nozzle 14 are composed of a material selected to achieve a pressure-release condition at any point between and including the inner and outer boundaries of the walls as experienced by the sound field in the liquid. Preferentially that is done by ensuring that the acoustical space in the conical body 4 and the nozzle 14 which has the characteristics close to the liquid (in terms of both the real and imaginary parts of the acoustical impedance that an infinite volume of the material would have), has a perimeter from which acoustical signals in the liquid are reflected with a pressure amplitude reflection coefficient (R) close to −1, −0.95 to −1.0, preferably from −0.99 to −1.0. That is to say, almost all the incident energy is reflected back into the liquid, with a 180 degree phase change occurring in the pressure waveform on reflection. That perimeter can be at the interface between the liquid and the solid wall, or in the wall, or at the interface between the wall and the outer atmosphere, depending on the choice for the real and imaginary parts of the specific acoustic impedance of the material(s) which make up the wall. This pressure-release condition is achieved by providing that the conical body 4 and the nozzle 14 thereof have a pressure amplitude reflection coefficient (R) with respect to the acoustic energy in the aqueous liquid, i.e. water or a saline solution, within the chamber 9 of from −0.95 to −1.0, preferably from −0.99 to −1.0.

When the liquid stream containing acoustically excited gas bubbles leaves the nozzle 14, there is an interface between the liquid stream and air. The pressure amplitude reflection coefficient (R) with respect to the acoustic energy in a semi-infinite volume of aqueous liquid, i.e. water or a saline solution, at the water/air interface, would be −0.999. That is to say, in general there is an acoustic impedance mismatch (i.e. poor impedance matching) between aqueous liquid and air. However when a material is bounded in a shape and size, with walls of a certain material and thickness, that volume of itself has an acoustic impedance. It is very important not to confuse these different impedances. The objective of the device is to avoid impedance mismatches between the sound fields in the conical body 4, the nozzle 14 and the stream, so that energy propagates from transducer 22 into the liquid within the conical part 5 of the central chamber 6 and thence into the nozzle part 7 of the central chamber 6 defined by the nozzle 14 and thence into stream, with minimal losses, notably at the interfaces between these three acoustical compartments. One way of matching them is to ensure that the specific acoustic impedance of the material that houses the sound field, and the acoustical boundary conditions at the perimeter of that sound field, and the shape and size of that acoustical perimeter; match. If an acoustical modal structure exists, that modal structure must be appropriate to the transmission of energy from transducer 22 to conical part 5 to nozzle part 7 to stream to target.

Consequently, in order to provide that the acoustic energy in the stream, and in the gas bubbles in the stream, is not absorbed by the conical wall or nozzle, the pressure-release boundary condition of the sound field in the cone (either the liquid in the cone alone or the combination of the liquid and the cone) must match the pressure-release boundary condition between the liquid and atmospheric air. This means that one of three cases needs to be satisfied. The first case that satisfies the required conditions is that in which the boundary between the liquid and the wall material has a reflection coefficient (R) of approximately zero, the wall material does not attenuate acoustic waves significantly, and the reflection coefficient (R) between the wall material and the atmospheric air is the same as that between the liquid and atmospheric air. The second case that satisfies this condition is when the pressure amplitude reflection coefficient (R) with respect to the liquid and the nozzle wall material is substantially the same as the pressure amplitude reflection coefficient (R) with respect to the acoustic energy in the aqueous liquid at the liquid/air interface. Performance in this second case is augmented if the pressure amplitude reflection coefficient (R) with respect to the liquid and the cone wall material is substantially the same as the pressure amplitude reflection coefficient (R) with respect to the acoustic energy in the aqueous liquid and the nozzle wall material. The third case that satisfies this condition is when the nozzle material is engineered in such a way as to provide a pressure amplitude reflection coefficient (R) at some intermediate location between the inner and outer wall that is substantially the same as the pressure amplitude reflection coefficient (R) with respect to the acoustic energy in the aqueous liquid at the liquid/air interface. Performance in this third case is augmented if the cone material is engineered in such a way as to provide a pressure amplitude reflection coefficient (R) at some intermediate location between the inner and outer wall (which smoothly transitions to the respective location of the corresponding boundary in nozzle) that is substantially the same as the pressure amplitude reflection coefficient (R) with respect to the acoustic energy in the aqueous liquid at the liquid/air interface. Consequently, the conical body 4 and the nozzle 14 provide a pressure amplitude reflection coefficient (R) with respect to the acoustic energy in the aqueous liquid, i.e. water, at some point within boundary of chamber 9 which is as close to −1 as possible, in particular from −0.95 to −1.0, preferably from −0.99 to −1.0.

The conical wall and nozzle are shaped such that, at the tip of the nozzle where the stream leaves the nozzle, the perimeter of the pressure release boundary in the nozzle is identical to the perimeter of the outer radius of the liquid stream at the moment that it leaves the nozzle.

The substantially conical element may be geometrically conical, or alternatively may have a non-geometric shape, such as being horn-shaped or bell shaped. The substantially conical element may be formed, for example, of cellular foam, plastic, rubber, or a composite of materials. Cellular foam, if its specific acoustic impedance is much less than that of the liquid (which is likely if it much less dense than the liquid), will place a pressure release reflection coefficient (as seen by the acoustic energy that is propagating in the liquid towards that interface) at the inner boundary of the cone and nozzle, where the liquid meets the solid. Alternatively, if the substantially conical element has a specific acoustic impedance that is similar to that of the liquid, then the pressure release boundary will occur between the solid wall and the outer atmosphere. Note that this requires that the solid material used does into absorb too much acoustical energy, or this will violate the condition that the acoustical energy which returns to the liquid after reflection is substantially the same as the acoustical energy which attempted to propagate out of the liquid. Other materials, including glasses and plastic, may be used provided they also satisfy the following criteria (i.e. that an acoustic wave heading towards the material from the water eventually (i.e. from the inner surface of the wall, the outer surface of the wall, or some structure embedded within the wall) produces a reflection back into the water that substantially contains all the energy present in the original waveform, but with the pressure wave inverted by 180 degrees in phase. The choice of material is determined by the requirement to match (as closely as practicable) the acoustic wall boundary conditions at the edge of the ultrasonic field within the cone to those at the edge of the acoustic field in the nozzle and those at the edge of the ultrasonic field in the liquid stream once it leaves the nozzle, so as to avoid sharp impedance mismatches between cone, nozzle and liquid stream that would hinder the passage of acoustic energy along the stream from the transducer, through the cone and into the nozzle, through the nozzle and into the stream.

Therefore, a design principle employed by the conical body 4 and the nozzle 14 used in the preferred embodiments of the present invention is that the acoustic boundary condition at the edge of the acoustic field in the cone and nozzle (which will be at the inner wall if the wall material is, say, much less dense that the liquid; and at the outer wall if the specific acoustic impedance of the wall is sufficiently similar to that of water and the wall materials do not significantly absorb the sound) should match the acoustic boundary condition that will occur in the stream of liquid once it leaves the nozzle. Other materials, including glasses and plastic, may be used provided they also satisfy the following criteria i.e. that an acoustic wave heading towards the material from the liquid eventually (i.e. from the inner surface of the wall, the outer surface of the wall, or some structure embedded within the wall) produces a reflection back into the water that substantially contains all the energy present in the original waveform, but with the pressure wave inverted by 180 degrees in phase.

In use, liquid flows continuously through the supply conduit 20 into the central chamber 6 and then outwardly through the outlet 16 of the nozzle 14 to form a stream 24 of liquid which is directed against the surface 26 of tissue 28 to be treated. The surface 26 may, in particular, be provided with three dimensional surface features, such as a crevice 30 shown in an exaggerated form in FIG. 1, which forms an anatomical pocket.

A bubble generator 32 may be located within the conical body 4 upstream, in the direction of fluid flow, of the outlet nozzle 14 and the orifice 12 therein. The bubble generator 32 generates gas bubbles within the liquid stream so that the liquid stream impacting on the surface 26 includes not only acoustic energy from the transducer 22 but also gas bubbles which have been acoustically excited by the acoustic energy from the transducer 22. Preferably a bolus of bubbles is formed in each of a series of treatment cycles. In each treatment cycle, the respective bolus of bubbles is directed to the target surface, and then, when located at the target surface, is acoustically excited. In this specification the term "bolus of bubbles" is intended to mean a plurality of bubbles that are close together, and form a small, tight cloud of bubbles in the liquid.

There are several options for seeding gas bubbles into the liquid flow, including gas injection and in situ electrochemical gas bubble generation by electrochemical decomposition of water in the liquid. For in situ electrochemical gas bubble generation, the incorporation of electrodes, for example 10-100 μm diameter Pt wires, into the liquid flow allows controlled seeding. Alternatively, small bubbles of selected gases, such as oxygen or ozone, are generated close to the nozzle 14 by electrolysis, microfluidic injection, radiation, or ultrasonic or flow cavitation, etc. Electrolysis and microfluidic injection are preferred for achieving gas bubbles with the desired and controlled bubble size, in particular to prevent or restrict the formation of excess bubble dimensions. Electrolysis is particularly convenient if the aqueous solution contains salt to give it standard conductivity, as might be used in aqueous medical saline. A short electrical pulse can produce the spatially restricted bolus of small bubbles of a size that is roughly resonant with the sound field to be used for treatment of the target surface. Periodically reversing the current will reduce the decrease in electrode performance over time. If the conductivity of the liquid is low, conductivity (e.g. polymer) membranes between the electrodes can assist with electrolysis.

In the illustrated embodiment, the bubble generator 32 is located within the conical body 4. The liquid flow into the conical body 4 is pre-treated to remove gas bubbles from the liquid flow so that the bubbles controllably generated within the conical body 4 are the only bubbles present in the liquid stream to be acoustically excited. The pre-treatment also can remove solid particles from the liquid flow, and also some dissolved or suspended chemicals.

The liquid supply is a supply of clean water or saline solution. Throughout this specification, whether the skilled person wishes to use sterile liquid is a clinical decision in line with guidance: for example, sterile liquids are not usually used in the oral cavity, and in certain circumstances there are justifiable reasons for using clean but not sterile liquids in wound irrigation. Throughout this specification, where the liquid is mentioned, it should be understood that the assessment of whether to use sterile or simply clean liquid will be a clinical decision. This also includes whether the liquid contains drugs or antimicrobial ingredients. The temperature of the liquid supply may be regulated, and the liquid may have been degassed. The liquid supply is pumped to a desired pressure by a pump 27. Alternatively the liquid feed can be gravity fed from an elevated container, so that pump 27 is not needed: this can be particularly is resources are limited (e.g. pump facilities are not available), or if the skilled person wishes to reduce the possibility of a pump entraining unwanted large bubbles into the flow, and/or if the skilled person wishes to use pre-prepared (possibly sterile) bags of bottles of rinse, which could optionally have been degassed prior to sealing to reduce the need for an outgasser, as described below.

The pump outlet 29 passes to a venturi 31 which decreases the dissolved gas concentration within the liquid, by application of suction by the venturi and bubble buoyancy and coalescence. The degassed liquid is then fed to a liquid pressure control 33 which provides a sufficient liquid pressure to enable the liquid to flow at a desired flow rate through a subsequent outgasser 34 which is located upstream of the inlet 18 of the conical body 4. The outgasser 34 is configured to remove gas bubbles from the liquid flow.

The outgasser 34 comprises a casing 35 having an input 36 and an output 37. A plurality of compartments 38 are serially located between the input 36 and output 37 which define a serpentine path 39 therebetween. In the illustrated embodiment, the serpentine path 39 is vertically oriented, although other non-vertical orientations may be employed.

The input 36 is, in the figure, a downwardly oriented pipe 92 (although a horizontal inlet point would work equally as well) located at an upstream central part 93 of the outgasser 34 and the output 37 is located at a lower part 94 of the downstream end wall 95 in communication with a lower portion of a compartment 38. In the illustrated embodiment each compartment 38 is either circular, for the central first compartment 38, or annular, for the remaining radially outward second, third, etc compartments 38. The serpentine path 39 is annular, and extends radially outwardly.

By providing successive compartments 38 of increasing radius, the cross-sectional area of the flow from the compartments 38 along the outgasser 34 increases, which progressively slows down the flow rate along the outgasser 34, and correspondingly enhances the ability of larger bubbles to rise within the liquid flow and be separated from the liquid flow.

The annular arrangement is particularly attractive because each wall need only support a fraction of the overall pressure drop between input 36 and output 37, meaning the likelihood of leaks and overall weight and cost of materials can be reduced.

In an alternative configuration, the outgasser 34 comprises a linear array of the compartments 38; the input 36 is a downwardly oriented pipe located at an upstream central part of the outgasser and there are two outputs, each output being located at a lower part of respective opposite downstream end walls at opposite sides of the outgasser 34. There are two serpentine paths 39 extending in opposite linear directions. Each output 37 connects to a respective inlet 18 of the conical body 4, or connects to a common manifold which then connects to the inlet 18 of the conical body 4.

The apparatus may further comprise, at a location upstream of the input 36, in the direction of liquid flow into the casing, a venturi device for removing from the liquid gas in solution in the liquid. This venturi will increase the volume of gas required to be removed by the outgasser 34, but will ensure a lower dissolved gas content which will cause any bubbles that escape the outgasser to dissolve more quickly.

A heating device for heating the liquid may be located at a location upstream of the input 36, in the direction of liquid flow into the casing 35, and upstream of the venturi device if present. A cooling device for cooling the liquid may be additionally or alternatively located at a location downstream of the output, in the direction of liquid flow from the casing 35. By heating the aqueous liquid more gas comes out of solution, so this can enhance the performance by heating the water just before it enters the venturi or outgasser. By cooling the water, more gas tends to dissolve, so cooling the aqueous liquid as it exits the outgasser reduces uncontrolled gas bubble formation in the conical chamber.

The serpentine path 39 is, in use, filled with the liquid flow from the input 36 to the output 37. Each compartment 38 of the series of compartments 38 comprises an upstream chamber 40 and a downstream chamber 41. Each upstream chamber 40 defines an upward flow path 42 therealong and each downstream chamber 41 defines a downward flow path 43, with alternating upward flow paths 40 and downward flow paths 43 in combination forming the serpentine path 39.

Each pair of adjacent upstream and downstream chambers 40, 41 of each compartment 38 is separated by a respective first wall element 44 which extends upwardly from a bottom wall 45 of the casing 35. An upper edge 25 of the first wall element 44 is located lower than a top wall 46 of the casing 35 to define a headspace 47 thereabove.

Each pair of adjacent compartments 38 is separated by a respective second wall element 48 which extends downwardly from the top wall 46 of the casing 35. A lower edge 49 of the second wall element 48 is located above the bottom wall 45 of the casing 35 to define a fluid connection 90 between the adjacent compartments 38.

A filter element 91 is located within the fluid connection 90. The filter element 91 may be held in place by shaping of the lower edge 49 of the second wall element 48 and/or the bottom wall 45 of the casing 35, for example to define a channel for receiving the filter element 91 or to provide tooth elements which are embedded into the filter element 91.

The filter element 91 typically comprises a porous open cell foam or sponge, for example composed of a synthetic polymer, which may optionally be supported within a cage or by a framework. Alternatively, the filter element 91 comprises a porous ceramic or stone or plastic or fabric, or a metal mesh. The filter element 91 is configured to function to filter out gas bubbles exceeding a desired dimension. In addition, the filter element 91 is configured to filter out unwanted solid particles and dissolved or suspended chemicals in the liquid flow.

Baffle members 96, defining an array of parallel linear channels, may be provided within one or more of the compartments 38 to enhance laminar flow of the liquid through the outgasser 34 and reduce turbulence.

The serpentine path 39 extends from the input 36 upwardly into the first upstream chamber 40, over the upper edge 45 of the first wall element 44, downwardly into the first downstream chamber 41, through the first fluid connection 90 and the filter element 91 located therein, and thereby into the adjacent second compartment 38. This sequence is repeated for the series of compartments 38 until the output 37 is reached.

In use, the casing 35 is filled with liquid so that the liquid level extends above the upper edge 45 of each first wall element 44 but is below the top wall 46 of the casing 35 to provide a headspace 47 in each compartment 38 which contains gas and is free of liquid. Each headspace 47 is vented to provide an outlet for excess gas pressure within the headspace 47, for example by providing a gas conduit 97 connected to a common manifold pipe 98.

The liquid flow from the input 36 is caused to rise within the first upstream chamber 40, and passes over the upper edge 25 of the first wall element 44, then is caused to descend downwardly into the first downstream chamber 41, and through the first fluid connection 90 and the filter element 91 located therein, and thereby into the adjacent second compartment 38. This sequence is repeated for the series of compartments 38 until the output 37 is reached.

In the compartments 38, bubbles have greater buoyancy than liquid. Consequently, any bubbles tend to rise more rapidly than the liquid when the liquid is caused to rise within each first upstream chamber 40. When the liquid is caused to descend within each downstream chamber 41, the bubbles tend to descend more slowly than the liquid. The resultant effect is that the bubbles reach the liquid upper surface and then accumulate in the headspace 47 beneath the top wall 46, and the accumulated gas is vented away by the gas conduits 97.

Each compartment 38 may optionally be provided with a capillary tube outlet in the top wall 46 to permit excess gas pressure venting but which prevents leakage of liquid. A liquid sensor may be provided to detect the liquid level in the compartment 38 to warn of actual or potential liquid leakage or overfilling of the compartments 38, or to activate a vent when the gas content in the headspace exceeds a predetermined limit, as monitored via liquid level sensing, ballcock, conductivity sensor, optical sensor, ultrasonic level meter or equivalent. The headspaces 47 may be in fluid communication to ensure gas pressure equalisation within the outgasser 34. However some embodiments have advantages in isolating each headspace 47 one from another, for example if there is a possibility that the outgasser 34 might be tipped at an angle. At least one wall of the casing may be transparent, e.g. composed of a transparent polymer sheet, to permit viewing of the liquid levels to check correct operation of the outgasser 34. The casing 34 may be at least partially disassembled for cleaning, maintenance or filter replacement. An additional filter may be located within the output 37.

Accordingly, the outgasser 34 functions to remove gas bubbles from the liquid flow so that within the liquid flow entering the conical body 4 for formation of gas bubbles of a controlled size and excitation of the gas bubbles by the acoustic transducer 22, there are substantially no gas bubbles of an undesired excess dimension, and the void fraction of bubbles smaller than this is so low as to not noticeably reduce the performance of the device for example by absorbing or scatter the sound field in the cone and nozzle. Consequently, the liquid stream exiting the nozzle 14 has a gas bubble population having a controlled size distribution and in particular a threshold for the maximum bubble size, so that the flow contains only bubbles smaller than this, and furthermore has a controlled void fraction that is not so large as to degrade the performance of the device. Furthermore it is advantageous to restrict the spatial spread of bubbles to a small bolus of bubbles that travels down the stream, with substantially bubble-free water flowing in front of and behind this bolus as it travels towards the target tissue.

The operation of the outgasser 34 can readily be tuned to control the threshold for the maximum bubble size of any bubbles present in the liquid flow entering the conical body 4 by adjusting the liquid flow rate through the outgasser 34 (which can be done by choice of the way the widening of the annuli reduces the flow), or alternatively it can be done by stacking outgassers in series so that the outflow of one enters a second as its inflow.

Therefore in the illustrated embodiment, the venturi 31 and the outgasser 34 are employed to prevent large bubbles from being present in the liquid stream, and to ensure that the void fraction of bubbles entering the stream (other than bubbles purposefully placed in the stream by the bubble generator) is not so great as to impede the liquid flow and acoustic transmission in the path of the ultrasound from the transducer to the target tissue via the cone, nozzle and stream.

However, in some embodiments of the present invention in which the diameter of the liquid stream is selected to be large, for example greater than approximately 10 mm, and the ultrasonic frequency is lower than approximately 200-300 kHz, this in turn permits a resonant gas bubble size to be selected so that larger bubbles sizes that may be inadvertently present in the liquid flow into the conical body do not significantly reduce the effectiveness of the cleaning, healing and tissue regeneration effect of the acoustically excited bubbles (depending on the gassiness of the liquid flow provided e.g. by water mains, bagged or bottled liquid, etc.). In such embodiments, either or both of the venturi 31 and the outgasser 34 may be omitted. However, when small resonant bubble dimensions are required for an effective cleaning, healing and tissue regeneration effect of the acoustically excited bubbles, for example with a low volume flow rate of the stream and a low stream width, then at least one of, and preferably both of, the venturi 31 and the outgasser 34 may be required to pre-treat the aqueous liquid stream, the likelihood of their being needed as the frequency increases, and the likelihood being reduced if other steps are taken to reduce the likelihood of bubbles in the liquid feed (e.g. sealed bottles or bags of degassed fluid are sufficiently elevated to provide a gravity fed supply without the need for a pump).

In an alternative embodiment, the bubble generator 32 is located upstream, in the direction of fluid flow, of the liquid supply conduit 20.

In an alternative embodiment, the conical body 4 and nozzle 14 are composed of material that can function as a pressure release boundary when aqueous fluid is thereagainst, so that acoustic energy in the aqueous fluid is effectively and efficiently reflected with a phase change transmitted back into the flowing liquid at the inner surface of the conical body 4 and nozzle 14. The aim of the apparatus of this embodiment is to introduce acoustic energy into the flowing fluid stream and then to direct that stream through the outlet onto the surface to be treated by using the conical shape and outlet to concentrate both the acoustic energy and the fluid flow while minimising acoustic losses or frictional loses against the conical and outlet surfaces.

The rear wall 8 functions as a backplate which serves the acoustical purpose of transmitting the ultrasound from the transducer 22 into the liquid in the cone. It also puts distance between the edge of the transducer 22 and the pressure release boundary where the net pressure fluctuation is zero (because the incident acoustic wave is added to the phase inverted reflected pressure wave). Bringing that pressure release boundary close to the transducer 22 degrades the amplitude of the sound field that can be generated in the liquid close to the transducer 22.

A faceplate of the transducer 22 can be bonded onto the rear wall 8. Alternatively the transducer faceplate can be in direct contact with the liquid if the transducer accesses directly the liquid via a water-tight aperture in the backplate, so that if the transducer faceplate is flush with the side of the backplate in contact with the liquid, the backplate acts as a rigid acoustical baffle, amplifying the sound field in the liquid. Contact of the transducer with the liquid in this way can help the water to cool the transducer, as can the backplate if it has sufficient thermal conductivity. This can also work if the transducer is bonded onto the backplate without an aperture, as can the addition of a cooling coil to take the water supply, or a diverted offshoot from it, in a cooling coil which wraps around the transducer and is thermally connected to it. Measures to prevent the transducer heating up assist in keeping its performance stable, The embodiment discussed above is directed to the specific application of introducing sound energy into the liquid stream when the liquid is surrounded by air after leaving the nozzle. The nozzle and the outlet are shaped and dimensioned to allow for acoustic transmission along the fluid stream. It is advantageous to form a smooth flow of the stream. It is well within the abilities of a person skilled in the art to produce a suitable combination of shape and dimensions for the conical body and nozzle outlet to achieve the desired smooth flow of liquid containing acoustic energy from the transducer.

Figure 2:
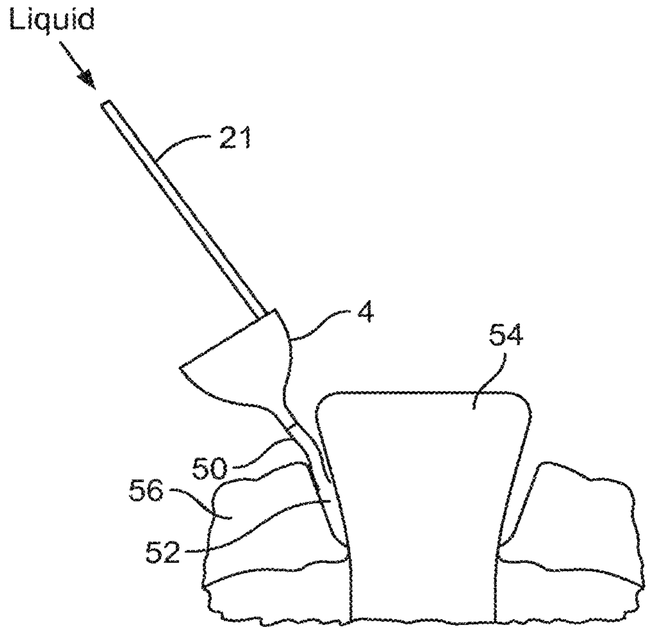
FIG. 2 is a schematic side view of a cleaning, healing and tissue regeneration apparatus in accordance with a second embodiment of the present invention.

In the embodiment of FIG. 2, the liquid stream 50 containing the acoustically excited gas bubbles is directed into a periodontal pocket 52 between a tooth 54 and gum tissue 56. The liquid stream typically clean water or clean saline solution for most oral procedures, except those where infection risk must be minimized commensurate with the current level of contamination and infection by bacteria or other micro-organism, and the susceptibilities of the tissue and patient. In this embodiment, the liquid stream 50 cleans the periodontal pocket 52 and promotes tissue healing and regeneration in the periodontal pocket. Therefore the liquid stream 50 can clean, and therapeutically treat, soft tissue. The liquid stream 50 can also clean hard tissue, such as the surface of the tooth 54, for example by removal or disruption of a biofilm on the tooth surface. Other dental sites such as root canals can also be cleaned and the soft tissue therein regenerated. Conventional dental tools or implements may optionally be used to open up the periodontal pocket 54 for cleaning and treatment.

Conventional dental suction devices may be employed to remove the run-off of the liquid stream, and to suck the liquid from the periodontal pocket and the oral cavity after the liquid has performed a cleaning/treating function against the soft and hard tissue surfaces to be treated. The removed liquid run-off may be stored for disposal or subsequent analysis. For example, the removed liquid run-off from the oral cavity may be analysed to determine the composition of the liquid, for example to target subsequent therapeutic treatment, such as drug or pharmaceutical therapy. Other anatomical structures that would be similarly treated include sinuses, ear canal, the digestive and the genito-urinary systems, and anatomical spaces or potential spaces in general or particular (e.g. as in the eye).

Figure 3:
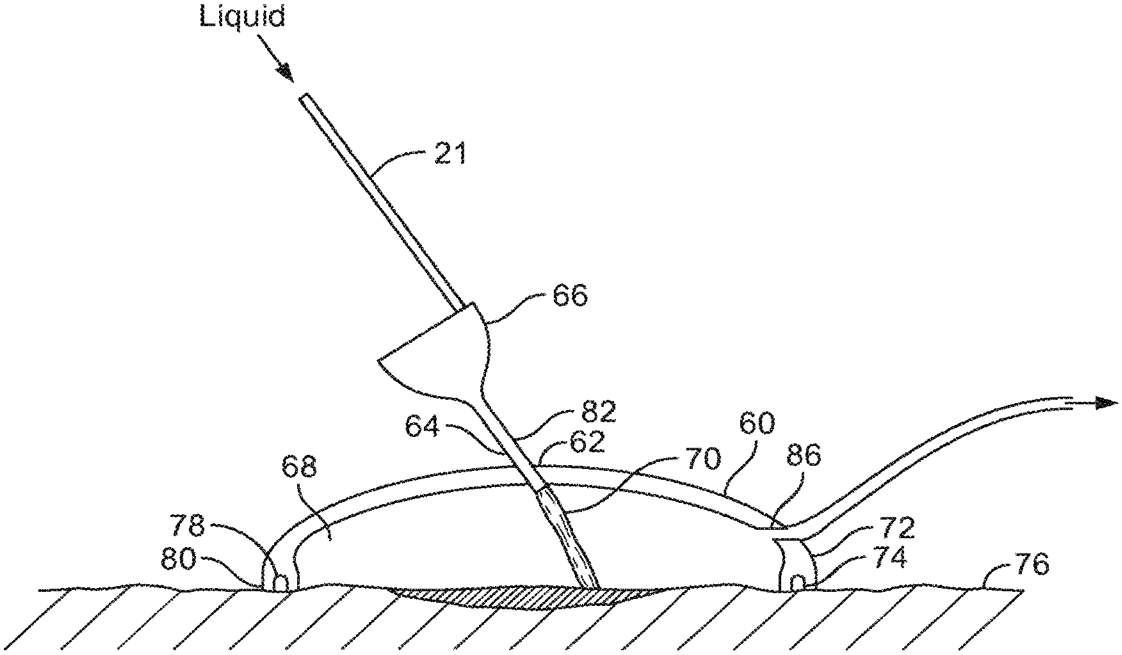
FIG. 3 is a schematic perspective view of a cleaning, healing and tissue regeneration apparatus in accordance with a third embodiment of the present invention.

Referring to the embodiment of FIG. 3, the apparatus is modified as compared to the apparatus of FIGS. 1 and 2 by providing a cup member 60 having a closed end 62 fitted to the outlet nozzle 64 of the conical body 66. The cup member 60 defines a second chamber 68. The cup member 60 is configured to receive the output stream 70 from the outlet nozzle 64 into the second chamber 68 from the closed end 62. The outlet nozzle 64 typically has a circular outlet orifice. The cup member 60 has an open end 72 with an annular rim 74 configured to form an annular contact against human tissue 76. Typically, the annular rim 74 is adapted to form an annular seal against the human tissue 76, and the annular rim 74 may, for example, include an annular groove, chamber or pocket 78 therein to provide an annular suction device 80 for sealing against the tissue 76.

The cup member 60 and outlet nozzle 64 are configured so that an orientation of the outlet nozzle 64 relative to the cup member 60 is modifiable thereby to modify the direction of the output stream 70 within the second chamber 68. Typically, the cup member 60 is composed of a flexible material, optionally a thermoplastic elastomer, or inert synthetic rubber. In one preferred configuration, additionally or alternatively, outlet nozzle 64 is translationally movable within the cup member 60. Typically, the outlet nozzle 64 and the cup member 60 are connected by a seal 82 therebetween.

The cup member 60 includes at least one outlet port 86 for liquid which communicates with, and extends away from, the second chamber 68.

In the embodiment of FIG. 3, the liquid stream 70 containing the acoustically excited gas bubbles is directed at a desired direction though the second chamber 68 of the cup member 60 and against a wound that is at least partially covered by the cup member 60. The liquid stream 70 typically comprises sterile water or a sterile saline solution. The cup member 60 allows the direction of the liquid stream 70 to be aimed at a desired region of the tissue to be treated, by orienting the outlet nozzle 64 at a desired angle and translationally moving the outlet nozzle 64 within the cup member 60. The annular rim 74 of the cup member 60 forms and maintains a seal between the cup member 60 and the skin/tissue/organ surface which reduces, minimises or prevents loss of liquid from the treatment site covered by the cup member 60. The annular rim 74 may be held against the skin by suction, for example using the annular groove/pocket 78 to provide annular suction for sealing against the tissue 76. Additionally or alternatively, the entire cup member 60 can be subjected to an underpressure, or a pressure which is less than atmospheric pressure, for example by using a suction pump to reduce pressure within the second chamber 68, so that atmospheric pressure applies a holding pressure on the cup member 60 against the tissue 76. In such circumstances flow control (e.g. valves, pressure differentials and gradients) would be needed to ensure satisfactory forward flows, and no backflows, through orifice 86 and the nozzle outlet 64.

In this embodiment, the liquid stream 70 cleans the soft tissue and the wound. The liquid stream 70 can clean the wound by removing at least one of a contaminant, unwanted particulate matter, a microbe, a biofilm, and a chemical from the wound. The liquid stream 70 can also clean the wound by disrupting a tissue-bound biofilm in the wound or anatomical pocket. Furthermore, the liquid stream 70 treats the wound by healing the wound, such as by stimulating blast cells in tissue in the wound, for example by causing, promoting or enhancing re-epithelialisation of epidermal tissue in the wound, such as by stimulating dermal fibroblasts and keratinocytes in epidermal tissue in the wound and modulating mediators of tissue repair, or similarly regenerating an organ to replace the normal tissue that would have occupied that location when the organ was healthy.

The run-off of the liquid stream 70 is removed though the outlet port(s) 86. The run-of may passively flow through the outlet port(s) 86. Alternatively, suction from a suction pump may be applied to remove the liquid run-off though the outlet port(s) 86. The removed liquid run-off may be discarded directly, stored for disposal or subsequent analysis, or be taken for immediate analysis. For example, the removed liquid run-off from the wound treatment may be analysed to determine the composition of the liquid, for example to detect microbial species, to detect biofilm components or composition, or to target subsequent therapeutic treatment, such as drug or pharmaceutical therapy.

The outflow from the cup can be disposed of; or alternatively sent for measurement tests to provide a rapid diagnosis. Such a rapid diagnosis would be extremely valuable, because if the injury contains a bacterial biofilm, then if an effective treatment can be applied within 24 hours of the ultrasonic disruption of the biofilm (indeed, the sooner the better within that 24 hour window), it can be far more effective at healing the wound and combatting the infection than if the same treatment is applied after the 24 hour window after disruption of biofilm. Ironically, guidelines which insist on rapid treatment of infection in order to save lives in the short term, might indeed put lives in danger in the longer term by promoting the use of broad-spectrum antibiotics, if the guideline window for treatment does not allow sufficient time to identify the microbe present and any resistances it has. A rapid diagnosis based on the run-off from the wound would reduce this hazard. Similar comments apply for other forms of microbe.

When the apparatus of the preferred embodiments of the present invention is employed to treat human or animal tissue, the liquid supply system 21 is adapted to supply a liquid flow through the inlet at a flow rate of from 0.1 to 7 litres/minute, optionally from 0.1 to 0.75 litres/minute, for example from 0.25 to 0.5 litres/minute. Typically, the outlet nozzle 14 is configured to generate an output stream of liquid flow having an average width of from 0.25 to 20 mm, optionally from 0.25 to 10 umm, further optionally from 0.25 to 4 mm, for example from 0.5 to 2 mm. The acoustic transducer 22 is configured to generate acoustic energy having a frequency of from 0.1 to 5 MHz, for example from 0.5 to 5 MHz. The gas bubble generator 32 is configured to provide in the output stream bubbles having a radius of from 0.5 to 40 μm, optionally from 0.6 to 20 μm for example from 0.75 to 4 μm. Note however that the flow rate, stream diameter, frequency, optimal and maximum permissible bubble sizes and void fractions, and the amplitude of the sound field at the target tissue, cannot be independently selected, and instead the choice of one of these (starting with the front of this list and working forwards) narrows down the possible range of values from which one might select items later in the list.

For example, in human dental or for wound treatment on a hospital ward, the volume flow rate, or flux, of liquid to the site of interest may advantageously not exceed 0.3 litres/min. If, for example, the site were the mouth, then greater flow rates would generate acceptance problems with dental patients. If the treatment site is a wound, for example on human skin, greater flow rates would produce volumes of run-off that would be inconvenient to handle. Moreover, there may be an enhanced risk of spillage of infectious material with increasing flow rates. However flow rates up to much higher values, for example 5 litres per minute, might be acceptable for wound treatment in large animals in a zoo situation.

Furthermore, one advantage of having low flow rates is that the run-off may be collected and used for subsequent diagnostic analysis. For example, the analysis may be for an infection by bacteria or other micro-organism, such as with an objective to meet a 24 hour time window within which a correct antibiotic would be effective against a disrupted biofilm. When such an analysis is employed, the volume of post-rinse run-off liquid should not be inconveniently large, resulting in the microbial load being inconveniently dilute, which would mitigate against easy handling, analysis and diagnostics.

For a given liquid flow rate, this parameter correspondingly impacts on the dimensions of the width or cross-section of the liquid stream. Since the flow speed cannot fall below a minimum speed without the stream breaking up and preventing the sound passing down it to reach the wound, to meet the criterion of the selected flow rate the width dimension, for example the average width, which is the diameter for a circular cross-section stream, of the liquid stream must be selected to provide the desired flow rate without the risk of breaking up the stream. With a flow rate of about 0.3 Litres/min, the diameter is typically around 1 mm. Larger flow rates allow for commensurately wider streams.

For a given average width of the liquid stream, this parameter in turn correspondingly impacts on the ultrasonic frequency of the acoustic energy. The average width corresponds to a minimum threshold for the ultrasonic frequency otherwise the ultrasound would be evanescent in the liquid stream, and the acoustic energy would not propagate in the liquid stream to the target tissue/wound/pocket. For a stream average diameter which is typically around 1 mm, the ultrasonic frequency is preferably at least 1 MHz.

For a given ultrasonic frequency of the acoustic energy, this parameter in turn correspondingly impacts on the gas bubble radius. The ultrasonic frequency corresponds to the dimensions of the bubbles on which the Faraday waves and other surface waves on the bubble wall need to be stimulated. For an ultrasonic frequency which is at least 1 MHz, typically the effective gas bubbles are about 1 μm in radius. The actual optimal bubble size is that which experiences resonance pulsation with the sound field frequency, which can be calculated once the gas and liquid parameters are known (e.g. liquid density, static pressure etc.) noting that once the bubbles are smaller than about 30 microns in radius, it is important for most bubbles not to neglect the influence of surface tension in determining the pulsation resonance bubble size for a given ultrasonic frequency. Significantly larger bubbles than this optimal bubble size (e.g. bubbles having radii more than 10% greater than the radius of the bubble that is in pulsation resonance with the ultrasonic frequency) would tend to degrade the sound field.

For a given bubble dimension, it should be provided that bubbles larger than the desired radius (the radius that is resonant with the sound field, i.e. 1 micron radius for a sound field of, say, 3 MHz), are absent from the liquid stream, while at the same time ensuring, for example by microfluidic or electrolytic bubble generation, that there are bubbles of the desired radius, for example 1 μm, present in order to host the surface waves. For example, the liquid flow may be treated to remove bubbles larger than a selected radius.

This combination of parameters provides the advantage that small bubbles can, through the action of flow and acoustic radiation forces, penetrate smaller crevices than can larger bubbles.

Bubbles of pulsation resonance size are useful for cleaning, healing and tissue regeneration, but larger bubbles degrade the cleaning/healing/regeneration effect, because they scatter and absorb the sound field without contributing to the cleaning, healing and tissue regeneration. This attenuates the acoustic power that would otherwise reach the resonant bubbles, and so hinders cleaning, healing and tissue regeneration. Therefore it is vital to remove such larger bubbles from the flow. This can be achieved by a Venturi, an outgasser, and/or the use of degassed water. Any or all can be used, though if not all can be used, the outgasser is preferred unless the skilled person has access to adequate supplies of degassed water which can be fed into the device without entraining bubbles.

For a selection of an ultrasonic frequency and bubble dimension, the acoustic driving pressure can be increased to enhance the achievement of surface waves at the bubble wall. Furthermore, salts, such as sodium chloride, and surfactants may be provided in the liquid stream to selected to modify the surface properties, for example the surface tension, of the bubble wall and enhance the achievement of surface waves at the bubble wall.

Furthermore, the flow speed of the liquid stream will have an influence on the existence and effect of Rayleigh perturbations in the liquid stream, which tend to generate narrowing in the stream. The cut-off frequency for the stream waveguide is determined by the dimension of the narrowest part of the stream, and so such Rayleigh perturbations would tend to reduce the ability of ultrasonic acoustic energy in the MHz range to travel down the stream. The option of increasing the ultrasonic frequency, to be above the cut-off frequency for the narrowest part of the stream, is not an option, because that would require a commensurate decrease in the bubble size (from 1 μm to, for example, 0.1 μm radius), and this would produce difficulties in generating Faraday surface waves at the bubble wall. Consequently, the ultrasonic frequency cannot be freely increased, and so the generation of the Rayleigh perturbations in the stream must be controlled by providing a selection of flow rate, flow speed and stream width as discussed above.

Various example scenarios showing how maximum and minimum parameters may be calculated are shown in Table 1. Some of these parameters are dictated by the laws of physics, and some of these parameters may, for example, constitute preferred practical upper or lower limits. These examples employ calculations for a variety of wound cleaning, healing and tissue regeneration applications. The example calculations are made assuming air bubbles in clean water with no added salts at room temperature under 1 bar of static pressure.

TABLE 1

| Column 1 Volume Flow Rate (L/min) | Column 2 Min Radius (mm) | Column 3 Max Radius (mm) | Column 4 Min operating frequency ($\times10^3$ Hz) | Column 5 Max operating frequency ($\times10^3$ Hz) | Column 6 Optimal bubble radius (mm) | Column 7 Max bubble radius (mm) | Column 8 Min operating pressure at the target tissue (dB re: 1 μPa) | Column 9 Max operating pressure at the target tissue (dB re: 1 μPa) |
|---|---|---|---|---|---|---|---|---|
| 0.2 | 0.39 | | 1464 | | 0.00250 | (0.00275) | 207.9 | 222.0 |
| | 0.39 | | | (7320) | 0.00050 | (0.00055) | 211.7 | 227.5 |
| | | 1.43 | 396 | | 0.00910 | (0.01001) | 200.6 | 220.7 |
| | | 1.43 | | (1982) | 0.00180 | (0.00198) | 211.6 | 222.6 |
| 1 | 0.87 | | 655 | | 0.00550 | (0.00605) | 208.1 | 211.0 |
| | 0.87 | | | (3273) | 0.00110 | (0.00121) | 218.8 | 224.0 |
| | | 10.9 | 52 | | 0.06940 | (0.07634) | 181.5 | 220.2 |
| | | 10.9 | | (261) | 0.01387 | (0.01526) | 199.4 | 220.5 |
| 3 | 1.5 | | 378 | | 0.00956 | (0.01052) | 200.2 | 220.7 |
| | 1.5 | | | (1890) | 0.00191 | (0.00210) | 210.8 | 222.5 |
| | | 22.62 | 25.1 | | 0.14430 | (0.15873) | 117.0 | 220.2 |
| | | 22.62 | | (125) | 0.02886 | (0.03175) | 190.5 | 220.3 |
| 5 | 1.94 | | 293 | | 0.01235 | (0.01359) | 199.3 | 220.5 |
| | 1.94 | | | (1464) | 0.00247 | (0.00272) | 207.9 | 222.0 |
| | | 31.8 | 17.8 | | 0.20284 | (0.22312) | 171.4 | 220.1 |
| | | 31.8 | | (89.1) | 0.04057 | (0.04463) | 190.6 | 220.2 |

In the column marked Column 1, a number of different aqueous liquid flow rates are indicated. In the method of the invention, a flow rate is selected to match the particular application, for example an oral care application for a human patient in which the liquid stream is applied into the mouth at a flow rate which is sufficiently low to avoid flooding the mouth with the aqueous liquid.

Column 2 specifies the minimum width or radius of the stream (note this is the radius, i.e. half the diameter if the stream perimeter is circular). The minimum radius of the stream is calculated from the flow rate. The minimum stream radius follows from the requirement to avoid the production of a high pressure jet, since a low pressure stream of aqueous liquid is desired in the method of the invention, for example having a maximum stream pressure of 50 kPa, which substantially corresponds to 0.5 atm pressure. Here we refer to the pressure generated by the flow of the stream itself on the target (which must not be confused with the acoustic pressure of the ultrasonic field, or the radiation pressure, or the pressure within the bubble, or the pressure waves radiated by a cavitation event). Such pressures in the flow exceed 50 kPa in the least powerful pressure/power washers, where the pressure and flow in the stream are the mechanism used in cleaning. The present invention seeks to avoid unwanted damage to the wanted tissue from such pressures, and instead generate cleaning, healing and tissue regeneration using the effects of non-inertial cavitation.

Column 3 specifies the maximum radius of the stream, based on the requirement for stream stability, to avoid it breaking up into drops or undergoing narrowing and distortion by large instabilities, as discussed above.

For each stream radius, there is a minimum and maximum operating frequency. The minimum operating frequency shown in Column 4 is based upon the acoustic cut-off, below which sound will not travel down a stream with pressure-release walls as seen from the sound field in the water, as discussed above.

There is no firm basis for stating a maximum operating frequency, and the values given in Column 5 are based on a practical solution of multiplying the minimum frequency by a factor of 5. Unlike the minimum operating frequency (Column 4), these maximum operating frequency values are not constraining, or based on the laws of physics, but are a practical solution a single transducer is used to drive the sound field, placing a limit of the energy at roughly the 5$^{th}$ harmonic of the fundamental (note that an integer of 5 here only roughly represents the actual frequency multiplier for this circular stream, because the actual multiplier would be based on the appropriate Bessel function). Because these values are not based on the laws of physics, for illustrative purpose the values in Column 5 are placed in brackets.

Column 6 shows the optimal bubble radius, for the corresponding frequency stated in the same row in Column 4 or Column 5). This parameter is dependent on the pulsation resonance of the bubble for the frequency in question. An operating frequency between the upper and lower frequencies stated in Columns 4 and 5 may be chosen, but note that there are there are 2 upper and 2 lower frequencies for each value of the flow rate initially selected in Column 1 at the start of the parameter determination process. Therefore by stating an optimal bubble size, it is important to note that that optimal size is a one-to-one mapping that directly follows from the frequency used. If a mode frequency between the upper and lower limits is chosen, then the optimal bubble size will be some value between those limits stated in Table 1, directly as a consequence of the operating frequency being changed, for example to suit the choice of an optimal acoustic field in the cone, or the transducer resonance, or (most likely) both.

Column 7 shows the maximum bubble radius, which is a calculated approximation. The optimal bubble radius is given by the pulsation resonance of the bubble for the frequency in question. Bubbles significantly larger than this will degrade the sound field by scattering. Therefore it is an advantage to ensure that no bubbles larger than 110% of the resonance bubble radius (which would correspond to 100% on this scale) are present. However the extent to which large bubbles degrade the sound field depends on their void fraction (the proportion by volume of bubbly water that is free gas), and a very low void fraction might enable bubbles as large as 140% to be present and still allow operation of the device. Just as with Column 6, if the operating frequency takes a value between the maximum and minimum values allowed in Table 1 for a given flow rate and stream radius, then the maximum bubble radius will change accordingly.

The optimal bubble size (Column 6) is in pulsation resonance with the sound field, and that conditions corresponds to there being a minimum acoustic pressure of that resonant sound field that will be required to simulate Faraday waves on that optimally-sized bubble. This minimum acoustic pressure at the target tissue is given in Column 8 and can be calculated. If the surface to be treated is a delicate but desirable structure (e.g. healthy tissue to be retained undamaged, which is often the case but not necessarily if a surgeon wishes to generate debridement), then it is desirable to avoid inertial cavitation, and that places an upper acoustic pressure on the sound field at the target tissue, as listed in Column 9. As with Columns 6 and 7, if the ultrasonic frequency is selected to be some intermediate value between the minimum (Column 4) and maximum (Column 5) values (in order to tune the transducer resonance to the frequency of a desirable sound field mode, for example), then the optimal bubble size will vary between the limits shown for the stream in question, and the minimum (Column 8) and maximum (Column 9) acoustic pressure amplitudes will need to be calculated within the ranges shown.

From Table 1, some desired parametric combinations for the aqueous liquid stream and entrained acoustically excited bubbles can be specified for different given ranges of volume flow rate of the liquid stream. These are shown in Table 2.

TABLE 2

| Volume Flow Rate (L/min) | Stream width (mm) | Operating frequency ($\times 10^3$ Hz) | Bubble radius (mm) |
|---|---|---|---|
| 0.1 to 0.5 | 0.75 to 4 | 375 to 7500 | 0.0005 to 0.02 |
| >0.5 to 2 | 1.5 to 30 | 50 to 3500 | 0.001 to 0.08 |
| >2 to 4 | 3 to 50 | 25 to 2000 | 0.002 to 0.15 |
| >4 to 6 | 3.5 to 75 | 17 to 1500 | 0.003 to 0.25 |

As an additional preferred mechanism to generate bubbles, electrochemical bubble seeding technology has been developed. Pulsed bubble generation (creating a bubble swarm) in tandem with pulsed acoustic excitation may generate 'active' bubbles on the surface to be cleaned, healed and regenerated. An amplitude or frequency modulated sound field, coupled with the acoustic energy optionally being switched on and off, may be employed to maximise the acoustic pressure delivered by the apparatus to the surface to be treated in the presence of a suitable bubble swarm. Such independent control can vary the bubble pulses and the acoustic energy pulses independently so that at the surface to be treated the bubbles and the acoustic energy pulse can be incident on, or in the vicinity of, the surface substantially simultaneously to enable efficient treatment of the substrate by the acoustic energy causing non-inertial cavitation of the bubbles at or in the vicinity of the surface.

Such pulsing of the acoustic energy does not need necessarily to turn the sound field off between pulses, but instead may modulate the acoustic energy, by amplitude or frequency modulation, it to provide high energy acoustic pulses separated by low energy background.

In some embodiments, the sound is turned off as the bubble swarm travels down the stream (to prevent acoustically-induced bubble coalescence), and then the sound is turned on to provide a modulated acoustic energy pulse once the bubble swarm reaches the surface to be treated. Once these bubbles have undertaken some treatment and started to disperse in the flow, the sound is turned off and another swarm of bubbles is generated at the nozzle and the process is repeated.

It is critically important to ensure that pulsing of the sound field and the bubble generation are coordinated to satisfy the following two rules:

The sound is not activated to achieve cleaning or healing when the bubbles are anywhere (in nozzle, stream etc.) except at, or very close to, the location where it is intended to treat the tissue. Otherwise bubbles in the water (even optimally-sized bubbles) attenuate the passage of the sound from the transducer to the target tissue; and the sound field causes the bubbles to coalesce to a size that is greater than the maximum allowed bubble radius. This means that the off-time of the pulsed acoustic field corresponds to the time taken for the tight bolus of bubbles produced by the bubble generator to travel in the flow from the bubble generator to the target tissue (e.g. 30-600 ms, where greater cleaning ranges require longer times, but faster flow speeds reduce this).

The sound to achieve cleaning or healing is timed to come on just as the bolus of bubbles reaches the location where it is expected that the target tissue is located, and to persist until the bubbles have largely stopped delivering beneficial effects to the target tissue. This means that the sound pulse intended to achieve cleaning or healing persists for around 50 ms.

The independent control can be achieved by taking into account the fact that sound travels down the liquid stream at a different speed to the bubbles. The timing of the current supplies used to generate bubbles and sound is such as to ensure both bubble swarm and ultrasound arrive at the surface at the same time. Given this criterion, the different transit times of bubbles and sound down the tube dictate the timing for the activation of the currents which generate sound and bubbles, such that their activations may be staggered if the timing so dictates. The underlying technical concept is to utilise their different transit times down the liquid stream to ensure that the bubbles and acoustic energy occur at the same time at the surface which is to be treated.

A preferred control protocol for the transducer 22 and bubble generator 32 is illustrated in FIG. 19. In FIG. 19, the relationship between voltage supplied to the transducer and to the bubble generator (the electrolysis wires; the pump or solenoid for introducing bubbles into the flow by microfluidics or Venturi) are shown on a common time axis for a pair of successive treatment cycle, each cycle providing a pulse of acoustically excited bubbles against the target surface.

In a first phase 100, the voltage is off and the transducer is not activated. In a second phase 102, a short signal 104 activates the bubble generator to produce a tight bolus (i.e. a small cloud) of bubbles that can then travel down the flow with relatively bubble-free water before and after it.

In a third phase 106, no ultrasound or bubbles are generated. This third phase 106 ensures that no sound propagates down the stream while bubbles are propagating down the liquid in the flow towards the target tissue. In this third phase 106 the liquid flow carries the bubbles towards the target surface located downstream of the nozzle outlet.

In a fourth phase 108, which is initiated at the moment the bubbles reach the target surface, the ultrasound is activated. In FIG. 19, the envelope 110 of the nearly sinusoidal signal emitted by the transducer is shown as the fourth phase 108. The transducer 22 is activated at a frequency which is close to the resonant frequency of the bubbles and close to a resonance of the transducer. The acoustic energy acoustically excites the bubbles at the target surface to be treated, and preferably generates surface waves in the bubble walls. The bubbles exhibit non-inertial cavitation at the target surface, providing the desired effects on the surface as discussed above.

Then the cycle of first to fourth phases is repeated to providing a successive cycle in which a further bolus of bubbles is generated and travels in the flow towards target surface. After the fourth phase 108, there is a successive first phase 100 during which the transducer is not activated which allows the bubbles and tissue to be flushed away from the wound/tissue.

By increasing the time period of the third phase 106, prior to initiation of the acoustic excitement of the bubbles at the target surface, targets at greater range from the transducer can be effectively treated. If the target surface is at a variety of ranges from the nozzle outlet, for example from 1 to 10 cm, then the time period for the third phase 106 can be correspondingly varied, either to provide a selected fixed time period for the third phase 106 or to provide a progressively changing time period for the third phase 106 over successive cycles. For example, in a sequence of cycles, the third phase 106 may have a progressively increasing time period to accommodate treatment at progressively increasing distances away from the nozzle outlet.

Note that it is particularly appealing to use one transducer to serve both functions, of generating the bubbles and undertaking cleaning and healing. In such circumstances there is no need of a bubble generator placed at location 32 in the nozzle, and that item 32 can be omitted as a separate item in the nozzle, because the transducer 22 now takes on its function, as well as retaining its former function of generating ultrasound to cause both cleaning and healing. This simplifies construction, though the off-times of the pulses that precede the pulses intended to cause cleaning and healing must be longer, because the bubbles must traverse not only the length of the liquid stream (as they did when the bubble generator was in the nozzle), but also the length of the nozzle and cone. The voltage applied to the transducer 22 to conduct both the bubble generation function and the cleaning and healing functions, is shown in FIG. 20. The preferred control protocol for the transducer 22 if it serves both as the bubble generator and as the source of the pulse for cleaning and healing, is illustrated in FIG. 20. In FIG. 20, the relationship between voltage supplied to the transducer and time is shown for a pair of successive treatment cycle, each cycle providing a pulse of acoustically excited bubbles against the target surface. Note that the line plotted in FIG. 20 is the envelope of nearly sinusoidal signals (or a summation of nearly sinusoidal signals).

Referring to FIG. 20, in a first phase 200, the voltage is off and the transducer is not activated. In a second phase 202, a short period high amplitude voltage pulse 204 activates the transducer. This generates a small cloud of bubbles. The frequency of the transducer activated in the second phase 202 may be at a lower frequency than the resonant frequency of the bubbles, and at a lower frequency than the resonant frequency of the transducer, because the purpose of the ultrasound in the second phase 202 is to generate bubbles rather than to acoustically excite the bubbles.

In a third phase 206, the transducer is not activated, and no ultrasound is generated. This third phase 206 ensures that no sound propagates down the stream while bubbles are in the chamber of the conical body or the nozzle. In this third phase 206 the liquid flow carries the bubbles towards the target surface located downstream of the nozzle outlet.

In a fourth phase 208, which is initiated at the moment the bubbles reach the target surface, the ultrasound is activated. In FIG. 19, the envelope 210 of the nearly sinusoidal signal emitted by the transducer is shown as the fourth phase 208. The voltage, and correspondingly the amplitude of vibration, may be different, e.g. lower, than in the second phase 202. The transducer is activated at a frequency which is close to the resonant frequency of the bubbles and close to a resonance of the transducer. The acoustic energy acoustically excites the bubbles at the target surface to be treated, and preferably generates surface waves in the bubble walls. The bubbles exhibit non-inertial vibration at the target surface, providing the desired effects on the surface as discussed above.

Then the cycle of first to fourth phases is repeated to providing a successive cycle in which a further pulse of acoustically generated bubbles is directed against the target surface. After the fourth phase 208, there is a successive first phase 200 during which the transducer is not activated.

By increasing the time period of the third phase 206, prior to initiation of the acoustic excitement of the bubbles at the target surface, targets at greater range from the transducer can be effectively treated. If the target surface is at a variety of ranges from the nozzle outlet, for example from 1 to 10 cm, then the time period for the third phase 206 can be correspondingly varied, either to provide a selected fixed time period for the third phase 206 or to provide a progressively changing time period for the third phase 206 over successive cycles. For example, in a sequence of cycles, the third phase 206 may have a progressively increasing time period to accommodate treatment at progressively increasing distances away from the nozzle outlet.

In any of the embodiments, the inlet 18 may be provided with an acoustic isolation device which prevents acoustic energy being transmitted back along the liquid supply conduit 20. The acoustic isolation device may comprise an acoustic filter, optionally having a selected frequency range, and/or a narrowing or expansion in the conduit 20, and/or an expansion chamber, and/or by control of the diameter of the conduit to provide that the driving frequency is below the cut-off frequency of all modes for the inlet (as would happen for sufficiently small-bore manifold inlets made of pressure-release material).

In these embodiments, the apparatus size can be varied to provide varying volumes of the liquid stream. Smaller or larger volumes can be achieved by scaling the flow rate, nozzle size and the driving acoustic frequency, thereby to provide an aqueous liquid stream impacted onto the surface accompanied by a suitable sound field and active bubbles.

The bubble generator 32 is adapted to generate gas bubbles which are then acoustically excited and impact on the surface to be cleaned, healed and regenerated. The bubbles are driven into oscillation by the acoustic energy and can get into crevices and pores on the substrate to be cleaned, healed and regenerated, so that they effectively clean, and stimulate healing and regeneration in, the substrate.

The bubble generator 32 may act directly to inject gaseous bubbles into the fluid flow, for example through a needle, the needle optionally vibrating. Other options for bubble generation include through use of cavitation (hydrodynamic or acoustic) or free-surface bubble entrainment, or chemical gas production, or by a more preferred route of electrochemical in situ generation of gas bubbles by electrolytic decomposition of the water in the liquid flow. If the liquid has low conductivity, conductive polymers can be placed between the electrodes. The bubble generator 32 adapted for electrochemical bubble generation comprises an electrode comprising an array of electrically conductive wires, for example platinum wires having a diameter of 50 μm, extending across the outlet, for when bubbles of around 20-30 μm radius are required. Commensurately smaller bubbles in general demand thinner wires, depending on the surface tension of the liquid. The electrode is connected to a source of electrical energy (not shown) and, when electrically powered, the electrical energy electrolytically decomposes water in the fluid flow to generate bubbles of both oxygen and hydrogen gas which are entrained in the flowing fluid and directed towards the target surface to be cleaned, healed, regenerated. Ozone generators can similar be operated and incorporated in this way.

The bubble generator may be controlled by a controller so that bubbles are formed intermittently to form boluses (intermittent swarms or waves) of bubbles which successively impact against the surface to be cleaned, healed, and regenerated. When the bubbles impact the surface to be cleaned/healed/regenerated, the bubbles are driven to oscillate by the acoustic energy, thereby penetrating crevices which are cleaned/healed/regenerated by the acoustic energy and the effect of the bubble non-inertial cavitation, particularly the surface waves on the bubble wall and the local shear and secondary waves that they generate in the surrounding local medium. It is particularly beneficial not to produce such swarms or boluses independent of the acoustic pulsing, but rather to coordinate the timing of the pulsing to the bubble generation and bubble generation systems as shown in FIG. 19, in order to ensure that:

One does not activate the sound to achieve cleaning or healing when the bubbles are anywhere (in nozzle, stream etc.) except at, or very close to, the location where one hopes to treat the tissue. Otherwise bubbles in the water (even optimally-sized bubbles) attenuate the passage of the sound from the transducer to the target tissue; and the sound field causes the bubbles to coalesce to a size that is greater than the maximum allowed bubble radius. This means that the off-time of the pulsed acoustic field corresponds to the time taken for the tight bolus of bubbles produced by the bubble generator to travel in the flow from the bubble generator to the target tissue (e.g. 30-600 ms, where greater cleaning ranges require longer times, but faster flow speeds reduce this).

The sound to achieve cleaning or healing is timed to come on just as the bolus of bubbles reaches the location where one expects the target tissue to be, and to persist until the bubbles have largely stopped delivering beneficial effects to the target tissue. This means that the sound pulse intended to achieve cleaning or healing persists for around 50 ms.

The amplitude or frequency modulated acoustic energy from the transducer may be pulsed intermittently. This produces pulses of acoustic energy, which interact with the intermittent bubble swarms described above, in a concerted manner.

The acoustic energy of the pulse activates the bubbles of the swarm at the surface to effect enhanced cleaning, and the stimulation of healing and tissue regeneration mechanisms, by non-inertial vibration of the bubbles at the surface, and optionally generating surface waves in the bubbles. This completes a cleaning (and the stimulation of healing and tissue regeneration mechanisms) cycle for a single bubble swarm. A next cleaning and therapy cycle for a subsequent bubble swarm is then initiated by generation of the subsequent bubble swarm.

At the nozzle there is a particular phase relationship between the generation of the sound pulse and the generation of the pulse of bubbles. The phase relationship changes as the sound and bubbles are transmitted away from the nozzle through the liquid since the acoustic energy and the bubbles are transmitted at different velocities through the liquid towards the surface to be cleaned, and in which healing and tissue regeneration processes are to be stimulated. The aim is to provide a phase relationship, which typically involves a delay time $t_d$ between bubble generation and generation of the pulse of the acoustic energy, so that the acoustic energy and the bubbles reach the surface to be cleaned (and in which healing and tissue regeneration processes are to be stimulated) in phase and at the same time.

Therefore by employing pulsed bubble generation and pulsed generation of acoustic energy in a coordinated manner, bubbles are excited at the surface so that bubbles are present at the surface when the acoustic energy is also at the surface, and furthermore the cleaning impact (and the stimulation of healing and tissue regeneration processes) achieved by both the bubbles and the acoustic energy is increased by additionally providing that the acoustic energy is amplitude or frequency modulated at a higher frequency that the pulses, greatly improving cleaning efficacy (and the stimulation of healing and tissue regeneration processes). The presence of a bubble swarm formed between a pair of acoustic energy pulses separates those acoustic energy pulses. Each bubble swarm is independently impacted on the surface to be treated and independently excited by the acoustic energy of the succeeding acoustic energy pulse.

In accordance with a further aspect of the apparatus and method of the present invention, it has been found that the addition of a surfactant to the liquid can affect the bubble size achievable without bubble coalescence. Sufficient surfactant may be added, if necessary, to prevent coalescence of bubbles as they flow down the stream if, without surfactant, such coalescence produces bubbles too large for appropriate cleaning (and the stimulation of healing and tissue regeneration processes); but not so much surfactant that the bubbles are too small for cleaning (or the stimulation of healing and tissue regeneration processes) when they reach the site.

The particular total surfactant and surfactant concentration values to achieve the desired bubble activity may be dependent on the type of surfactant employed.

The present invention will now be described in greater detail with reference to the following non-limiting Examples.

EXAMPLE 1

In this example, the cleaning of bacteria from a wound in animal and human tissue was investigated using the method and apparatus of the present invention.

In order to examine the therapeutic effect of an ultrasonically activated gas bubble-containing saline stream in accordance with the present invention on biofilm in biological soft tissue, a series of in vitro experiments were performed.

Two wound models were used: pig trotters obtained from a butcher (and so containing no remaining healing property); and a pre-wounded cultured human skin model (Epiderm™ FT, Mattek Inc, USA). The EpiDerm models were maintained in an antibiotic free medium under standard cell culture conditions at 37° C. and 5% CO2. Early stage biofilms were cultured within the wounds using fluorescent-tagged *Pseudomonas aeruginosa* pMF230 and SYTO-9 pre-stained E-MRSA-16.

Once established with biofilm, the wound models were rinsed with either a conventional saline wash (2 l/min) or an ultrasonically activated gas bubble-containing saline stream in accordance with the present invention (2 l/min), and residual bacteria within the wounds before and after treatments was visualised by direct in situ epifluorescence microscopy.

Following a one-minute or two-minute treatment (the text states which) with an ultrasonically activated gas bubble-containing saline stream in accordance with the present invention, a significant amount of biofilm was seen to have been removed from both models.

Figure 4A:
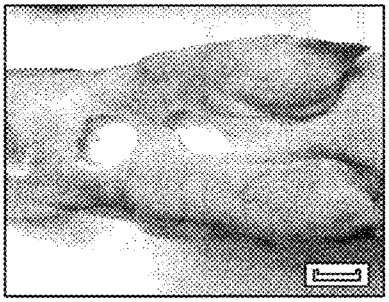
FIG. 4 shows images of a pig trotter wound model used in Example 1.
Figure 4B:
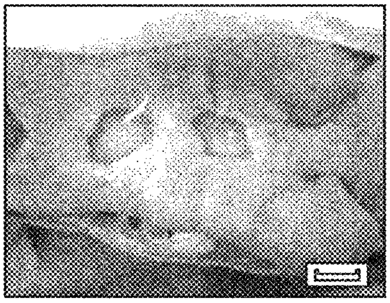
Figure 4C:
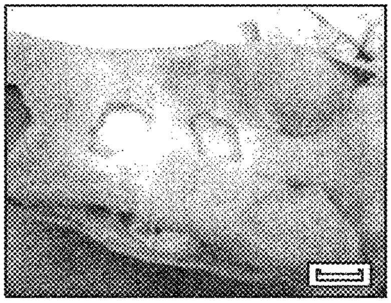

FIG. 4 shows images of the pig trotter wound model having ~2 cm diameter wounds produced within frozen/thawed pig trotters, before inoculation (A), post inoculation of *Pseudomonas aeruginosa* pMF230 and incubation at 37° C. for 5 hours (B) and post and wound beds post 2 min treatment by an ultrasonically activated gas bubble-containing saline stream in accordance with the present invention (C). Scale bars represent 2 cm.

Figure 5A:
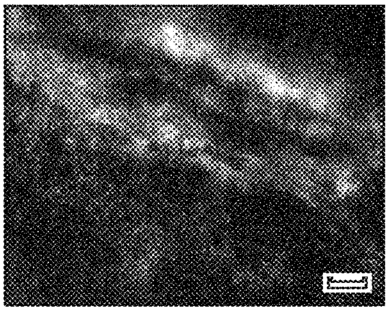
FIG. 5 illustrates micrographs which show direct EDIC/EF micrographs of SYTO-9 pre-stained E-MRSA-16 accumulation/early biofilm within the pig trotter wounds used in Example 1.
Figure 5B:
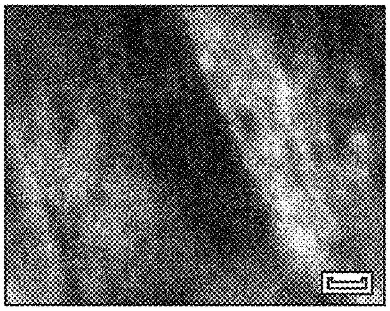
Figure 5C:
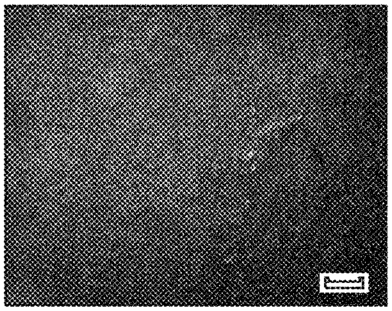
Figure 6A:
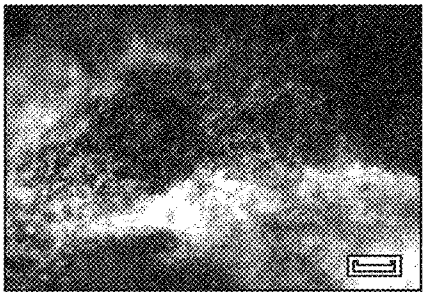
FIG. 6 illustrates micrographs which show *Pseudomonas aeruginosa* pMF230 in situ detection in direct EDIC/EF micrographs of GFP tagged *Pseudomonas aeruginosa* pMF230 accumulation/early biofilm within the pig trotter wounds used in Example 1.
Figure 6B:
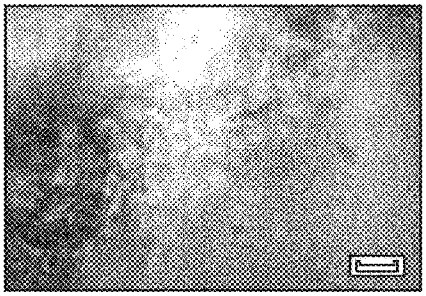
Figure 6C:
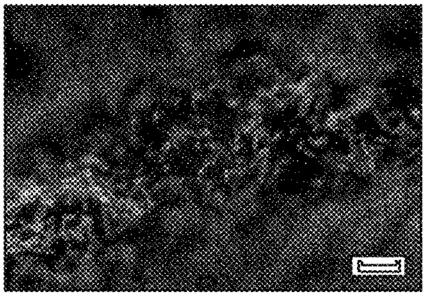
Figure 6D:
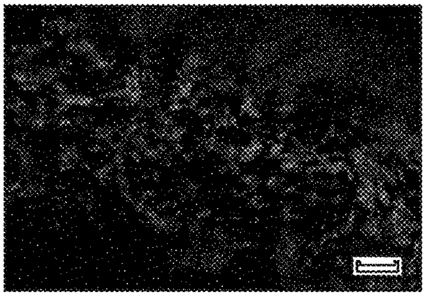

FIG. 5 shows direct EDIC/EF micrographs of SYTO-9 pre-stained E-MRSA-16 accumulation/early biofilm within the pig trotter wounds after 5 hour incubation at 37° C. This figure shows E-MRSA-16 in situ detection. FIG. 5 shows the results with no treatment (A), after a 1 min saline wash at a flow rate of 2 L/min (B) and after a 1 min treatment by an ultrasonically activated gas bubble-containing saline stream in accordance with the present invention at a flow rate of 2 L/min (C). Scale bars represent 10 sm.

FIG. 6 shows *Pseudomonas aeruginosa* pMF230 in situ detection in direct EDIC/EF micrographs of GFP tagged *Pseudomonas aeruginosa* pMF230 accumulation/early biofilm within the pig trotter wounds after 5 hour incubation at 37° C.; with no treatment (A), after a 1 min saline wash at a flow rate of 2 L/min (B), after a 1 min treatment by an ultrasonically activated gas bubble-containing saline stream in accordance with the present invention at a flow rate of 2 L/min (C) and after a 2 min treatment by an ultrasonically activated gas bubble-containing saline stream in accordance with the present invention at a flow rate of 2 L/min (D). Scale bars represent 10 μm.

Figure 7:
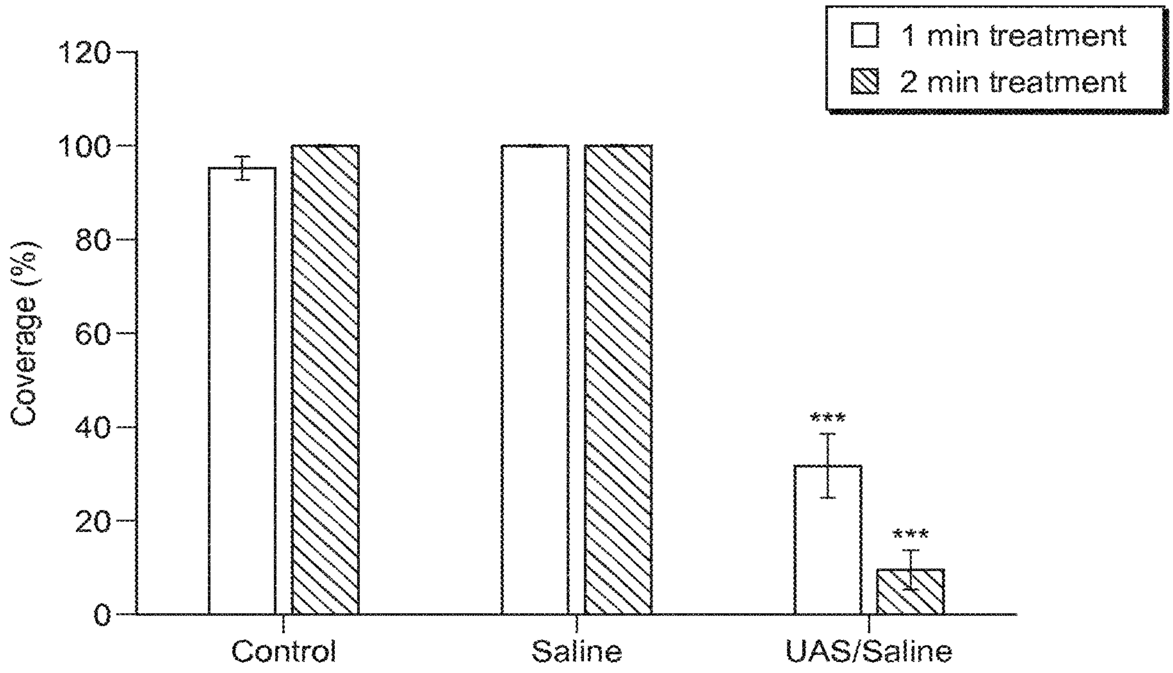
FIG. 7 is a graph which shows *Pseudomonas aeruginosa* pMF230 in situ detection image analysis, in particular image analysis (ImageJ) of EDIC/EF micrographs demonstrating the percentage coverage of GFP tagged *Pseudomonas aeruginosa* pMF230 accumulation/early biofilm within the pig trotter wounds used in Example 1.

FIG. 7 shows *Pseudomnonas aeruginosa* pMF230 in situ detection image analysis, in particular image analysis (ImageJ) of EDIC/EF micrographs demonstrating the percentage coverage of GFP tagged *Pseudomonas aeruginosa* pMF230 accumulation/early biofilm within the pig trotter wounds after 5 hour incubation at 37° C.; with no treatment (Control), after a 1 or 2 min saline wash at a flow rate of 2 L/min (Saline) and after a 1 or 2 min treatment by an ultrasonically activated gas bubble-containing saline stream (i.e. an ultrasonically activated stream (UAS) in accordance with the present invention at a flow rate of 2 L/min (UAS/Saline). Error bars represent the standard error of the mean (N=3), One way ANOVA/Tukey post hoc test demonstrated ***=p<0.001 when compared to the non-treated controls.

FIG. 8 shows *Pseudomonas aeruginosa* pMF230 in situ detection image analysis, in particular image analysis (ImageJ) of EDIC/EF micrographs demonstrating the percentage coverage of GFP tagged *Pseudomonas aeruginosa* pMF230 biofilm within the EpidermFT (Epiderm full thickness tissues (EFT), MatTek, USA) wound models after 24 hour incubation at 37° C. Data demonstrates % coverage straight (a) after treatment and (b) 24 hours post cleaning with no treatment (Control), after a 2 min saline wash at a flow rate of 2 L/min (Saline) and after a 2 min treatment by an ultrasonically activated gas bubble-containing saline stream in accordance with the present invention at a flow rate of 2 L/min (UAS/Saline). Error bars represent the standard error of the mean (N=3), One way ANOVA/Tukey post hoc test demonstrated=p<0.001 when compared to the non-treated controls.

These results illustrated in FIGS. 4 to 8 demonstrate that a wound treatment by an ultrasonically activated gas bubble-containing saline stream in accordance with the present invention is highly effective in removing bacterial biofilm from a living human cell wound model, without causing damage as shown by the normal microscopic architecture of the EFT skin model after treatment.

There is also an enhanced effect, with biofilm showing no regrowth at 24 hours post treatment.

This data suggests that wound treatment by an ultrasonically activated gas bubble-containing saline stream in accordance with the present invention is superior to conventional low frequency ultrasound (LFUS) systems used in wound care, where repeated applications and the use of biocides is often required to achieve lower levels of biofilm disruption than observed with the method of the present invention.

EXAMPLE 2

To explore whether wound treatment by an ultrasonically activated gas bubble-containing saline stream in accordance with the present invention had any effect on the rate of wound healing, a series of EpiDerm models, pre-wounded using a 3 mm punch biopsy, were treated with either a single plain saline wash or a single saline wash using an ultrasonically activated gas bubble-containing saline stream in accordance with the present invention.

The wounds were maintained under standard cell culture conditions, and samples of the culture media taken at day 0 and day 7 for analysis of matrix metalloproteinases (MMP1, 3, and 9) by enzyme immunoassay, as biochemical markers of fibroblast and keratinocyte activity in wound healing. At 7 days post treatment the wound sizes were calculated and the EpiDerm models were fixed in formalin and paraffin embedded. Transverse sections were prepared and stained with haematoxylin and eosin to permit basic histological examination Additional sections were prepared for immunohistochemical examination of fibroblast and keratinocyte activity and wound healing markers.

A reduction in wound diameter was seen in all EpiDerm models, showing that the models had remained viable throughout the time course of the experiment. No difference was observed between untreated control wounds and those treated with a plain saline wash.

However the wounds treated with an ultrasonically activated gas bubble-containing saline stream in accordance with the present invention showed a significant ($p=<0.01$) reduction in wound size, demonstrating a direct stimulation of healing.

FIG. 9 shows wound healing in the Epiderm full thickness wound models. These are example micrographs taken using a dissection microscope demonstrating the wound sizes 7 days post rinsing; with no treatment (A), after a 2 min saline wash at a flow rate of 2 L/min (B) and after a 2 min treatment by an ultrasonically activated gas bubble-containing saline stream in accordance with the present invention at a flow rate of 2 L/min (C). Scale bars represent 1 mm.

FIG. 10 shows wound healing in the Epiderm full thickness wound models, and is an image analysis results demonstrating the wound diameters 7 days post rinsing; with no treatment (Control), after a 2 min saline wash at a flow rate of 2 L/min (Saline) and after a 2 min wound treatment by an ultrasonically activated gas bubble-containing saline stream in accordance with the present invention at a flow rate of 2 L/min (UAS/saline). Error bars represent the standard error of the mean (N=3). One way ANOVA/Tukey post hoc test demonstrated $**=p<0.01$ when compared to the non-treated controls.

FIG. 11 shows Haematoxylin and Eosin (H&E) stained sections from the Epiderm full thickness wound models, in particular H&E stained sections (4 μm) taken from the EFT wounds 7 days post rinsing; with no treatment (A), after a 2 min saline wash at a flow rate of 2 L/min (B) and after a 2 min treatment by an ultrasonically activated gas bubble-containing saline stream in accordance with the present invention at a flow rate of 2 L/min (C and D). The arrows highlight the re-epithelialization across the wound bed. Scale bars represent 500 μm.

FIG. 12 shows the re-epithelialisation in the Epiderm full thickness wound models, the image analysis results demonstrating the distance of re-epithelialisation from the wound edge 7 days post rinsing; with no treatment (Control), after a 2 min saline wash at a flow rate of 2 L/min (Saline) and after a 2 min treatment by an ultrasonically activated gas bubble-containing saline stream in accordance with the present invention at a flow rate of 2 L/min (UAS/Saline). Error bars represent the standard error of the mean (N=3), T-test demonstrated $*=p<0.05$ when compared to the non-treated controls.

Histological examination confirmed no tissue damage following treatment by an ultrasonically activated gas bubble-containing saline stream in accordance with the present invention, and an increase in re-epithelization in wounds treated with treatment by an ultrasonically activated gas bubble-containing saline stream in accordance with the present invention compared to controls. Furthermore, immunohistochemistry showed stimulation of fibroblasts and keratinocyte migration in the wound models treated with an ultrasonically activated gas bubble-containing saline stream, as illustrated in FIGS. 13,14 and 15. Analysis of the cell culture medium showed modulation of matrix metalloproteinase activity in the wound models treated with an ultrasonically activated gas bubble-containing saline stream, particularly in the case of MMP9, demonstrating a direct action on dermal fibroblasts and keratinocyte migration to heal the wound, as illustrated in FIG. 16.

FIG. 13 illustrates micrographs showing immunohistochemical staining for cytokeratin 14 demonstrating stimulation of keratinocyte migration across wound following treatment by an ultrasonically activated gas bubble-containing saline stream in accordance with the present invention. Image analysis in graphical form demonstrates statistically significant increase in keratinocyte migration across the wound bed of the UAS treated epiderm models. Scale bars represent 500 μm and the error bars represent the standard error of the mean (SEM).

FIG. 14 illustrates micrographs of scans of the full wound bed demonstrating immunohistochemical staining of Cytokeratin 14 expressing keratinocytes. Full migration of the keratinocytes demonstrated in Epiderm full thickness tissues (EFT) samples 7 days post treatment with the UAS system.

FIG. 15(*a*) shows micrographs of immunohistochemical staining of fibroblasts with vimentin and FIG. 15(*b*) shows image analysis of the counts of immunohistochemical staining of fibroblasts in the dermo-epidermal junction of the treated EFT samples.

FIG. 16 is a graph showing modulation of matrix metalloproteinase 9 (MMP9) in the wound model culture medium, demonstrating modulation of MMP9 in models treated by an ultrasonically activated gas bubble-containing saline stream in accordance with the present invention.

These results show that that wound treatment by an ultrasonically activated gas bubble-containing saline stream in accordance with the present invention is able to stimulate human dermal fibroblasts, keratinocytes and modulate mediators of tissue repair.

EXAMPLE 3

To explore whether treatment by an ultrasonically activated gas bubble-containing saline stream in accordance with the present invention had any effect on the viability of biofilm causing bacteria, *P. aeruginosa* was inoculated onto stainless steel coupons, dried and then washed with saline or a saline wash using an ultrasonically activated gas bubble-containing saline stream in accordance with the present invention. Eluate was sampled, plated on agar and visualised using microscopy. Similarly, inoculated steel coupons were visualised using epifluorescence microscopy.

Examination of the steel coupons by epifluorescence microscopy showed no difference between uninoculated controls and inoculated coupons treated with an ultrasonically activated gas bubble-containing saline stream, demonstrating the ability to significantly remove bacterial contamination.

Further examination showed that the majority of *P. aeruginosa* removed by the ultrasonically activated gas bubble-containing saline stream were killed, demonstrating a bactericidal action.

FIG. 17 shows EDIC/EF micrographs demonstrating removal of *P. aeruginosa* from stainless steel coupons following washing with saline or a saline wash using an ultrasonically activated gas bubble-containing saline stream in accordance with the present invention (A=control, B=saline, C=ultrasonically activated gas bubble-containing saline stream).

FIG. 18 is a graph which shows killing of *Pseudomonas aeruginosa* using an ultrasonically activated gas bubble-containing saline stream in accordance with the present invention.

The invention claimed is:

1. A system for treating human or animal tissue, comprising:

a conical body defining a chamber, the conical body extending between a base of the conical body and an outlet nozzle of the conical body, wherein the base has an inlet for flow of a liquid into the chamber and the outlet nozzle is at a conical tip of the conical body and is adapted to generate an output stream of liquid flow from the chamber for treating human or animal tissue;

an acoustic transducer associated with the conical body and adapted to introduce acoustic energy into the liquid within the chamber whereby the acoustic energy is present in the output stream;

a gas bubble generator adapted for providing gas bubbles in the output stream that are adapted to be excited by the acoustic energy, wherein the conical body and the outlet nozzle are adapted to have pressure amplitude reflection coefficients with respect to the acoustic energy in liquid within the chamber of −0.95 to −1.0; and a liquid supply system adapted to supply the flow of the liquid through the inlet at a flow rate of 0.1 to 7 liters/minute, wherein the outlet nozzle is adapted to generate an output stream of liquid flow having an average width of 0.25 to 20 mm, wherein the acoustic transducer is adapted to generate acoustic energy having a frequency of 0.1 to 5 MHz, and wherein the gas bubble generator is adapted to provide, in the output stream, bubbles having a radius of 0.5 to 40 μm.

2. The system of claim 1, wherein the liquid supply system is adapted to supply the liquid flow through the inlet at a flow rate of 0.1 to 0.75 liters/minute.

3. The system of claim 1, wherein the outlet nozzle is adapted to generate the output stream of liquid flow having an average width of 0.25 to 10 mm.

4. The system of claim 1, wherein the acoustic transducer is adapted to generate acoustic energy having a frequency of 0.5 to 5 MHz.

5. The system of claim 1, wherein the gas bubble generator is adapted to provide, in the output stream, gas bubbles having a radius of 0.6 to 20 μm.

6. The system of claim 1, wherein the conical body and the outlet nozzle are adapted to have pressure amplitude reflection coefficients with respect to acoustic energy in liquid within the chamber of −0.99 to −1.0.

7. The system of claim 1, further comprising a cup member having a closed end fitted to the outlet nozzle of the conical body, the cup member defining a second chamber and is adapted to receive the output stream into the second chamber from the closed end, the cup member having an open end with an annular rim that is adapted to form an annular contact against human tissue.

8. The system of claim 7, wherein the cup member and the outlet nozzle are configured so that an orientation of the outlet nozzle relative to the cup member is modifiable to adjust a direction of the output stream within the second chamber.

9. The system of claim 7, wherein the cup member is composed of a flexible material.

10. The system of claim 7, wherein the annular rim is adapted to form an annular seal against human tissue.

11. The system of claim 10, wherein the annular rim includes an annular groove or chamber therein adapted to provide suction for sealing against tissue.

12. The system of claim 1, further comprising a controller for the acoustic transducer, wherein the controller is adapted to provide a plurality of sequential operating phases for the acoustic transducer, the phases comprising a bubble generating phase in which the acoustic transducer is activated to generate bubbles in liquid within the chamber, a rest phase in which the acoustic transducer is inactive to allow the generated bubbles to flow together with the output stream out of the output nozzle, and an acoustic excitation phase in which the acoustic transducer is activated to acoustically excite the bubbles which have flowed out of the output nozzle, that activation occurring at a moment when the bubbles reach a surface to be cleaned, healed or regenerated.

13. The system of claim 1, wherein the acoustic transducer is adapted to provide the gas bubble generator.

14. The system of claim 1, wherein at least one of the acoustic transducer and the gas bubble generator is configured to be controlled such that the frequency of the acoustic energy generated by the acoustic transducer is sufficient to produce non-inertial cavitation on bubble walls of the gas bubbles generated by the gas bubble generator.

15. The system of claim 14, further comprising a controller connected to the at least one of the acoustic transducer and the gas bubble generator, wherein the controller is adapted to control the at least one of the acoustic transducer and the gas bubble generator such that the frequency of the acoustic energy generated by the acoustic transducer is sufficient to produce non-inertial cavitation on bubble walls of the gas bubbles generated by the gas bubble generator.

16. The system of claim 1, further comprising a Venturi or an outgasser configured to remove gas bubbles having radii more than 10% greater than a bubble radius configured to be in pulsation resonance with the frequency of the acoustic energy.

17. A method of generating a liquid stream for treating human or animal tissue, comprising:

providing a conical body defining a chamber, the conical body extending between a base of the conical body and an outlet nozzle at a conical tip of the conical body;

inputting a flow of aqueous liquid into the chamber through an inlet at the base and generating an output stream of liquid flow from the chamber through the outlet nozzle, the output stream having a liquid flow rate of 0.1 to 7 liters/minute, and the output stream having an average width of 0.25 to 20 mm;

providing gas bubbles in the output stream, the gas bubbles having a radius of 0.5 to 40 μm;

introducing acoustic energy having a frequency of 0.1 to 5 MHz into the liquid within the chamber whereby the acoustic energy is present in the output stream and excites the gas bubbles, wherein the conical body and the outlet nozzle have pressure amplitude reflection coefficients with respect to the acoustic energy in the liquid within the chamber of −0.95 to −1.0; and directing the output stream comprising the acoustically excited gas bubbles and acoustic energy towards a surface to be treated.

18. The method of claim 17, further comprising controlling at least one of an acoustic transducer generating the acoustic energy and a gas bubble generator generating the gas bubbles such that the frequency of the acoustic energy generated by the acoustic transducer is sufficient to produce non-inertial cavitation on bubble walls of the gas bubbles generated by the gas bubble generator.

19. The method of claim 17, wherein the acoustic energy is introduced into the liquid using an acoustic transducer, further comprising controlling the acoustic transducer to generate the gas bubbles and to provide the gas bubbles in the output stream.

20. The method of claim 17, further comprising removing, from the liquid, gas bubbles having radii more than 10% greater than a bubble radius configured to be in pulsation resonance with the frequency of the acoustic energy.

* * * * *